US012059249B2

United States Patent
Shibata et al.

(10) Patent No.: US 12,059,249 B2
(45) Date of Patent: Aug. 13, 2024

(54) AUTHENTICATION DEVICE, AUTHENTICATION METHOD, AND RECORDING MEDIUM

(71) Applicant: NEC Corporation, Tokyo (JP)

(72) Inventors: Takashi Shibata, Tokyo (JP); Shoji Yachida, Tokyo (JP); Chisato Funayama, Tokyo (JP); Masato Tsukada, Tokyo (JP); Yuka Ogino, Tokyo (JP); Keiichi Chono, Tokyo (JP); Emi Kitagawa, Tokyo (JP); Yasuhiko Yoshida, Tokyo (JP); Yusuke Mori, Tokyo (JP)

(73) Assignee: NEC CORPORATION, Tokyo (JP)

( * ) Notice: Subject to any disclaimer, the term of this patent is extended or adjusted under 35 U.S.C. 154(b) by 610 days.

(21) Appl. No.: 17/280,448

(22) PCT Filed: Sep. 28, 2018

(86) PCT No.: PCT/JP2018/036352
§ 371 (c)(1),
(2) Date: Mar. 26, 2021

(87) PCT Pub. No.: WO2020/065935
PCT Pub. Date: Apr. 2, 2020

(65) Prior Publication Data
US 2022/0004609 A1    Jan. 6, 2022

(51) Int. Cl.
*H04L 9/00*    (2022.01)
*A61B 5/1171*    (2016.01)
(Continued)

(52) U.S. Cl.
CPC .......... *A61B 5/1171* (2016.02); *G06F 21/32* (2013.01); *G06V 10/267* (2022.01)

(58) Field of Classification Search
CPC ..... A61B 5/1171; A61B 5/0077; A61B 5/061; A61B 5/1032; G06F 21/32; G06V 10/267;
(Continued)

(56) References Cited

U.S. PATENT DOCUMENTS

2008/0235047 A1    9/2008    Broderick et al.
2013/0194407 A1    8/2013    Kim et al.
(Continued)

FOREIGN PATENT DOCUMENTS

JP    2000-139878 A    5/2000
JP    2002-279402 A    9/2002
(Continued)

OTHER PUBLICATIONS

International Search Report for PCT Application No. PCT/JP2018/036352, mailed on Dec. 25, 2018.
English translation of Written opinion for PCT Application No. PCT/JP2018/036352, mailed on Dec. 25, 2018.
Extended European Search Report for EP Application No. EP18935319.6 dated on Aug. 31, 2021.
Nguyen Kien et al. "Long range iris recognition: A survey", Pattern Recognition, vol. 72, Jul. 4, 2017 (Jul. 4, 2017), pp. 123-143.
(Continued)

*Primary Examiner* — Daniel B Potratz
*Assistant Examiner* — Syed M Ahsan

(57) ABSTRACT

An authentication device includes an image acquisition unit, an identification unit, and an authentication unit. The image acquisition unit acquires an image of an eye of a subject. The identification unit identifies the colored pattern of a colored contact lens worn by the subject by comparing a reference image with the image of the eye. The authentication unit identifies the subject, using a feature in a region other than a colored region of the colored pattern in the iris region of the eye.

13 Claims, 24 Drawing Sheets

(51) Int. Cl.
    *G06F 21/32* (2013.01)
    *G06V 10/26* (2022.01)

(58) Field of Classification Search
    CPC ...... G06V 20/52; G06V 40/19; G06V 40/193; G06V 40/197
    See application file for complete search history.

(56) References Cited

U.S. PATENT DOCUMENTS

| | | |
|---|---|---|
| 2015/0347841 A1 | 12/2015 | Mears |
| 2018/0197005 A1 | 7/2018 | Hunt et al. |
| 2018/0218212 A1* | 8/2018 | Yoshikawa .......... G06V 40/193 |
| 2020/0089951 A1* | 3/2020 | Inoue .................. G06V 40/197 |
| 2020/0097704 A1* | 3/2020 | Storm ................. G06V 40/172 |

FOREIGN PATENT DOCUMENTS

| | | |
|---|---|---|
| JP | 2006-343995 A | 12/2006 |
| JP | 2013-522754 A | 6/2013 |
| JP | 2018-124733 A | 8/2018 |

OTHER PUBLICATIONS

Doyle James S et al. "Automated classification of contact lens type in iris images", 2013 International Conference On Biometrics (ICB), IEEE, Jun. 4, 2013 (Jun. 4, 2013), pp. 1-6.

Baker S E et al. "Degradation of iris recognition performance due to non-cosmetic prescription contact lenses", Computer Vision and Image Understanding, Academic Press, US, vol. 114, No. 9, Sep. 1, 2010 (Sep. 1, 2010), pp. 1030-1044.

JP Official Communication for JP Application No. 2022-194571, mailed on Nov. 7, 2023 with English Translation.

* cited by examiner

Fig.3
| PRODUCT IDENTIFIER | COLORED PATTERN |
|---|---|
| P1 | 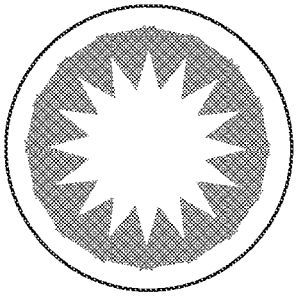 |
| P2 | 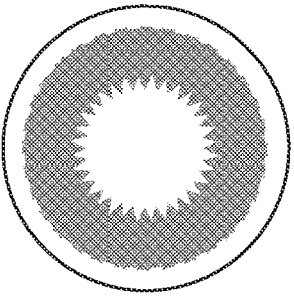 |
| ⋮ | ⋮ |
211 PRODUCT INFORMATION

Fig.4

221 AUTHENTICATION INFORMATION

| INDIVIDUAL IDENTIFIER | IRIS IMAGE (RIGHT EYE) | FEATURE VALUE (RIGHT EYE) | IRIS IMAGE (LEFT EYE) | IRIS IMAGE (LEFT EYE) |
|---|---|---|---|---|
| U1 | | FR1 | | FL1 |
| U2 | | FR2 | | FL2 |
| .. | .. | .. | .. | .. |

Fig.15

| INDIVIDUAL IDENTIFIER | PRODUCT IDENTIFIER | FEATURE VALUE OF CORRECTED IRIS REGION (RIGHT EYE) | FEATURE VALUE OF CORRECTED IRIS REGION (LEFT EYE) |
|---|---|---|---|
| U1 | P1 | FR'11 | FL'11 |
|  | P2 | FR'12 | FL'12 |
|  | : | : | : |
| U2 | P1 | FR'21 | FL'21 |
|  | P2 | FR'22 | FL'22 |
|  | : | : | : |
| : | : | : | : |

223 AUTHENTICATION INFORMATION

Fig.17

| PRODUCT IDENTIFIER | INDIVIDUAL IDENTIFIER |
|---|---|
| P1 | U1, U3, ... |
| P2 | U2, U5, ... |
| ⋮ | ⋮ |

231 WEARING INFORMATION

Fig.22

311 SURVEILLANCE INFORMATION

| INDIVIDUAL IDENTIFIER | NAME | SEX | CHARACTERISTICS |
|---|---|---|---|
| U1 | AAA | MALE | HEIGHT:170cm, WEIGHT:60kg |
| U2 | BBB | FEMALE | ... |
| ... | ... | ... | ... |

Fig.23

| PRODUCT IDENTIFIER | NOTIFICATION DESTINATION |
|---|---|
| P1 | S1, S2, S3, ... |
| P2 | S4, S5, S6, ... |
| ⋮ | ⋮ |

321 NOTIFICATION DESTINATION INFORMATION

AUTHENTICATION DEVICE, AUTHENTICATION METHOD, AND RECORDING MEDIUM

This application is a National Stage Entry of PCT/JP2018/036352 filed on Sep. 28, 2018, the contents of all of which are incorporated herein by reference, in their entirety.

TECHNICAL FIELD

The example embodiments relates to an authentication device, an authentication method, and a recording medium.

BACKGROUND ART

Iris authentication to authenticate individuals using an iris image is known. The iris that adjusts the opening diameter of the pupil has a pattern unique to each individual, and is said to remain unchanged throughout life. Therefore, by matching an iris image of a person to be authenticated against a previously registered iris image, the person can be authenticated. An example of a technique for reducing the influence of a contact lens worn by a person to be authenticated in such iris authentication is disclosed in, for example, PTL 1.

In the technique of PTL 1, a shadow region caused by a contact lens is detected, a corrected image with the shadow region removed from an iris image is generated, and authentication is performed using the corrected image.

CITATION LIST

Patent Literature

[PTL 1] JP 2000-139878 A

SUMMARY

Technical Problem

In recent years, colored contact lenses with a colored region provided in part of the contact lenses have been commercially available. Wearing colored contact lenses on eyes provides the decorative effect of changing the color of the irises and/or making the irises look larger, and thus colored contact lenses are increasingly popular. When a person to be authenticated is wearing colored contact lenses, an iris image of the person is different from a previously registered iris image, so that the authentication precision of iris authentication is reduced.

In the above-described technique of PTL 1, a method of removing a shadow region caused by a contact lens is disclosed. However, a method of reducing the influence of a colored contact lens itself is not disclosed.

It is an object of the example embodiments to provide an authentication device, an authentication method, and a recording medium that can prevent a reduction in the authentication precision of iris authentication even when a colored contact lens is worn.

Solution to Problem

An authentication device according to an aspect of the example embodiments includes an image acquisition means for acquiring an image of an eye of a subject, an identification means for identifying a colored pattern of a colored contact lens worn by the subject by comparing a reference image with the image of the eye, and an authentication means for identifying the subject, using a feature in a region other than a colored region of the colored pattern in an iris region of the eye.

An authentication method according to an aspect of the example embodiments includes acquiring an image of an eye of a subject, identifying a colored pattern of a colored contact lens worn by the subject by comparing a reference image with the image of the eye, and identifying the subject, using a feature in a region other than a colored region of the colored pattern in an iris region of the eye.

A computer-readable recording medium according to an aspect of the example embodiments causes a computer to execute a process including acquiring an image of an eye of a subject, identifying a colored pattern of a colored contact lens worn by the subject by comparing a reference image with the image of the eye, and identifying the subject, using a feature in a region other than a colored region of the colored pattern in an iris region of the eye.

Advantageous Effects

An advantageous effect of the example embodiments is to be able to prevent a reduction in the authentication precision of iris authentication even when a colored contact lens is worn.

BRIEF DESCRIPTION OF DRAWINGS

FIG. 3 is a diagram showing an example of product information 211 according to the first example embodiment.

FIG. 4 is a diagram showing an example of authentication information 221 according to the first example embodiment.

FIG. 15 is a diagram showing an example of authentication information 223 according to the third example embodiment.

FIG. 17 is a diagram showing an example of wearing information 231 according to the fourth example embodiment.

FIG. 22 is a diagram showing an example of surveillance information 311 according to the sixth example embodiment.

FIG. 23 is a diagram showing an example of notification destination information 321 according to the sixth example embodiment.

EXAMPLE EMBODIMENTS

Figure 1:
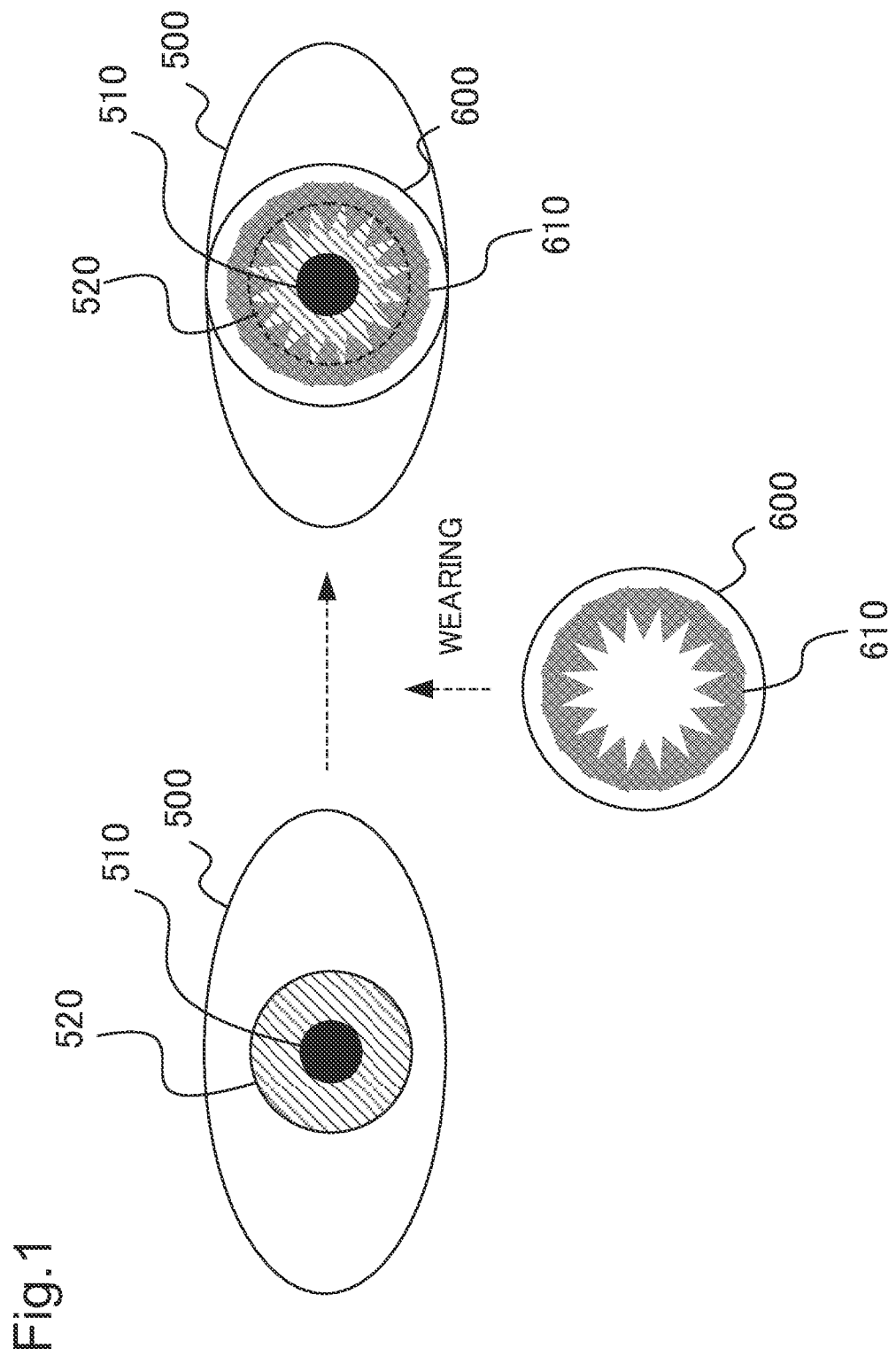
FIG. 1 is a diagram showing an example of wearing a colored contact lens.

Example embodiments will be described in detail with reference to the drawings. In the drawings and the example embodiments described in the description, the same reference numerals are assigned to the same or similar components to omit description of them as appropriate.

FIG. 1 is a diagram showing an example of wearing a colored contact lens. In FIG. 1, a colored contact lens 600 is worn on an eye 500. The eye 500 includes a pupil 510 and an iris 520. The colored contact lens 600 typically has a colored region 610 with an iris-mimicking colored pattern provided annularly in a position associated to the vicinity of the outer periphery of the iris 520 of the eye 500. A region other than the colored region 610 is transparent. Thus, on the eye 500 on which the colored contact lens 600 is worn, the vicinity of the outer periphery of the iris 520 is covered by the colored region 610.

In iris authentication, an image of the iris 520 when the colored contact lens 600 is not worn (hereinafter also referred to as an iris image) is registered. When a person to be authenticated is wearing the colored contact lens 600, an image of a combined region of the region of the iris 520 (hereinafter also referred to as an iris region) and the colored region 610 is used as an iris image.

First Example Embodiment

A first example embodiment will be described.

First, a configuration of an authentication system 1 according to the first example embodiment will be described.

Figure 2:
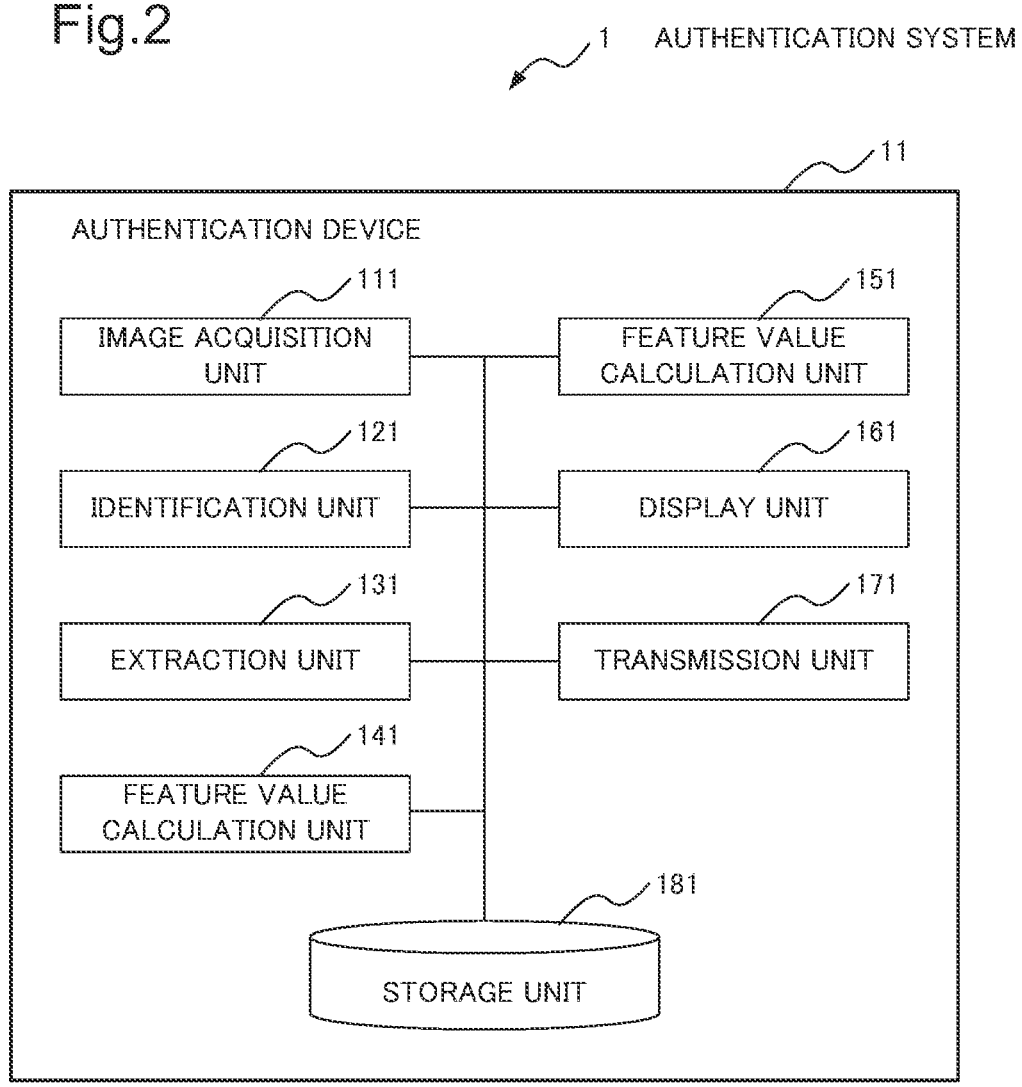
FIG. 2 is a functional block diagram of an authentication system 1 according to a first example embodiment.

FIG. 2 is a functional block diagram of the authentication system 1 according to the first example embodiment. The authentication system 1 includes an authentication device 11. The authentication device 11 includes an image acquisition unit 111, an identification unit 121, an extraction unit 131, a feature value calculation unit 141, an authentication unit 151, a display unit 161, a transmission unit 171, and a storage unit 181.

The image acquisition unit 111 acquires an image of an eye 500 of a subject of processing in the authentication device 11 (hereinafter also simply referred to as a subject).

The identification unit 121 compares reference images with the image of the eye 500 of the subject, to identify the colored pattern of a colored contact lens 600 worn by the subject.

In the first example embodiment, as the image of the eye 500 of the subject, an image of at least one eye 500 of both eyes 500 of the subject is used. As the reference images, images of the colored patterns of colored contact lens products (hereinafter also simply referred to as products) acquired from product catalogs, specifications, and the like of the products are used.

FIG. 3 is a diagram showing an example of product information 211 according to the first example embodiment. The product information 211 in FIG. 3 includes product identifiers "Pi" (i is, for example, an integer of one or more) for identifying colored contact lens products, and the colored patterns of the products associated with the product identifiers. The product information 211 is set in advance by an administrator or the like. Each product identifier may be the product model number, the product number, the serial number, the manufacturer's name, the product name, or a combination of them.

The extraction unit 131 extracts a corrected iris region 700 of the subject from the image of the eye 500 of the subject. The corrected iris region 700 is a region other than a colored region 610 of the identified colored pattern in the region of the iris 520 in the image of the eye 500.

The feature value calculation unit 141 calculates a feature value representing a feature of the corrected iris region 700 of the subject.

The authentication unit 151 matches the feature value of the corrected iris region 700 of the subject calculated by the feature value calculation unit 141 against feature values representing features of individuals' iris regions, to authenticate the subject. The feature value of each individual's iris region is calculated using an iris image acquired when a colored contact lens is not being worn on the individual's eye 500. The feature value of each individual's iris region is set in advance in authentication information 221 by an administrator or the like.

FIG. 4 is a diagram showing an example of the authentication information 221 according to the first example embodiment. The authentication information 221 in FIG. 4 includes individual identifiers "Uj" (j is, for example, an integer of one or more) for identifying individuals, and iris images of both eyes 500 of the individuals and feature values "FRj" and "FLj" calculated for the iris images, which are associated with the individual identifiers. The individual identifiers may be the individuals' names.

The authentication unit 151 may authenticate a subject using a determination device created by machine learning with feature values of individuals' iris regions as learning data.

The display unit 161 displays the authentication result to an administrator or the like.

The transmission unit 171 transmits the authentication result to another device or the like.

The storage unit 181 stores the product information 211 and the authentication information 221.

Figure 5:
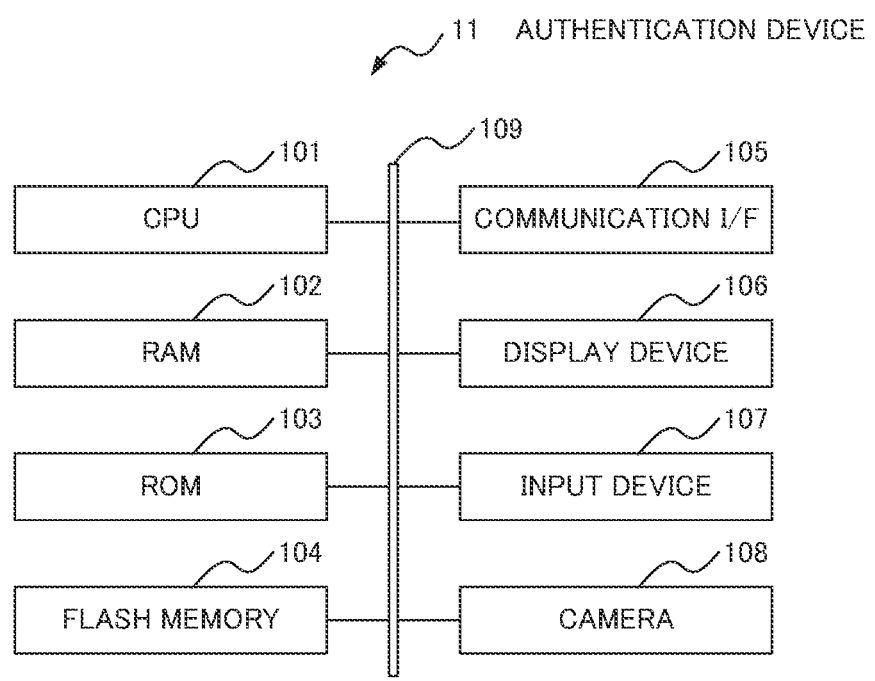
FIG. 5 is a block diagram showing an example of a hardware configuration of an authentication device 11 according to the first example embodiment.

FIG. 5 is a block diagram showing an example of a hardware configuration of the authentication device 11 according to the first example embodiment. The authentication device 11 is, for example, a mobile phone, a smartphone, a computer such as a personal computer (PC), or an information communication terminal.

The authentication device 11 includes a central processing unit (CPU) 101, a random-access memory (RAM) 102, a read-only memory (ROM) 103, and a flash memory 104. The authentication device 11 also includes a communication interface (I/F) 105, a display device 106, an input device 107, and a camera 108. The CPU 101, the RAM 102, the ROM 103, the flash memory 104, the communication I/F 105, the display device 106, the input device 107, and the camera 108 are connected to each other via a bus 109.

In FIG. 5, the components constituting the authentication device 11 are shown as an integrated device, but part of these functions may be constituted by an external device. For example, the camera 108 may be an external device different from a part constituting the functions of a computer including the CPU 101 and others.

The CPU 101 performs a predetermined operation according to programs stored in the ROM 103, the flash memory 104, etc., and controls each component of the authentication device 11. The RAM 102 is formed from a volatile storage medium, and provides a temporary memory area necessary for the operation of the CPU 101. The ROM 103 is formed from a nonvolatile storage medium, and stores necessary information such as programs used for the operation of the authentication device 11. The flash memory 104 is formed from a nonvolatile storage medium, and stores the product information 211 and the authentication information 221.

The communication I/F 105 is a module for performing wired or wireless communication with another device. The display device 106 is a display or the like, and displays moving images, still images, characters, etc. The input device 107 is a keyboard, buttons, a touch panel, or the like, and is used by an administrator or the like to operate the authentication device 11. The display device 106 and the input device 107 may be formed in one piece as a touch panel.

The camera 108 is, for example, a digital camera using a complementary metal-oxide semiconductor (CMOS) image sensor, a charge-coupled device (CCD) image sensor, or the like, and takes an image of a subject to acquire an image of an eye 500 of the subject.

Note that the hardware configuration shown in FIG. 5 is an example, and a device other than these may be added, or part of the devices may not be provided. Further, part of the devices may be replaced by another device having a similar function. Furthermore, part of the functions may be provided by another device via a network, or the functions constituting the example embodiment may be distributed among a plurality of devices to be implemented. For example, the flash memory 104 may be replaced by a hard disk drive (HDD), or may be replaced by a cloud storage.

The CPU 101 controls the camera 108 to implement the function of the image acquisition unit 111. The CPU 101 loads programs stored in the ROM 103 etc. into the RAM 102 and executes them, to implement the functions of the identification unit 121, the extraction unit 131, the feature value calculation unit 141, the authentication unit 151, and the transmission unit 171. The CPU 101 controls the display device 106 to implement the function of the display unit 161. The CPU 101 controls the flash memory 104 to implement the function of the storage unit 181.

Next, the operation of the authentication device 11 according to the first example embodiment will be described.

Here, it is assumed that the storage unit 181 stores the product information 211 in FIG. 3 and the authentication information 221 in FIG. 4.

Figure 6:
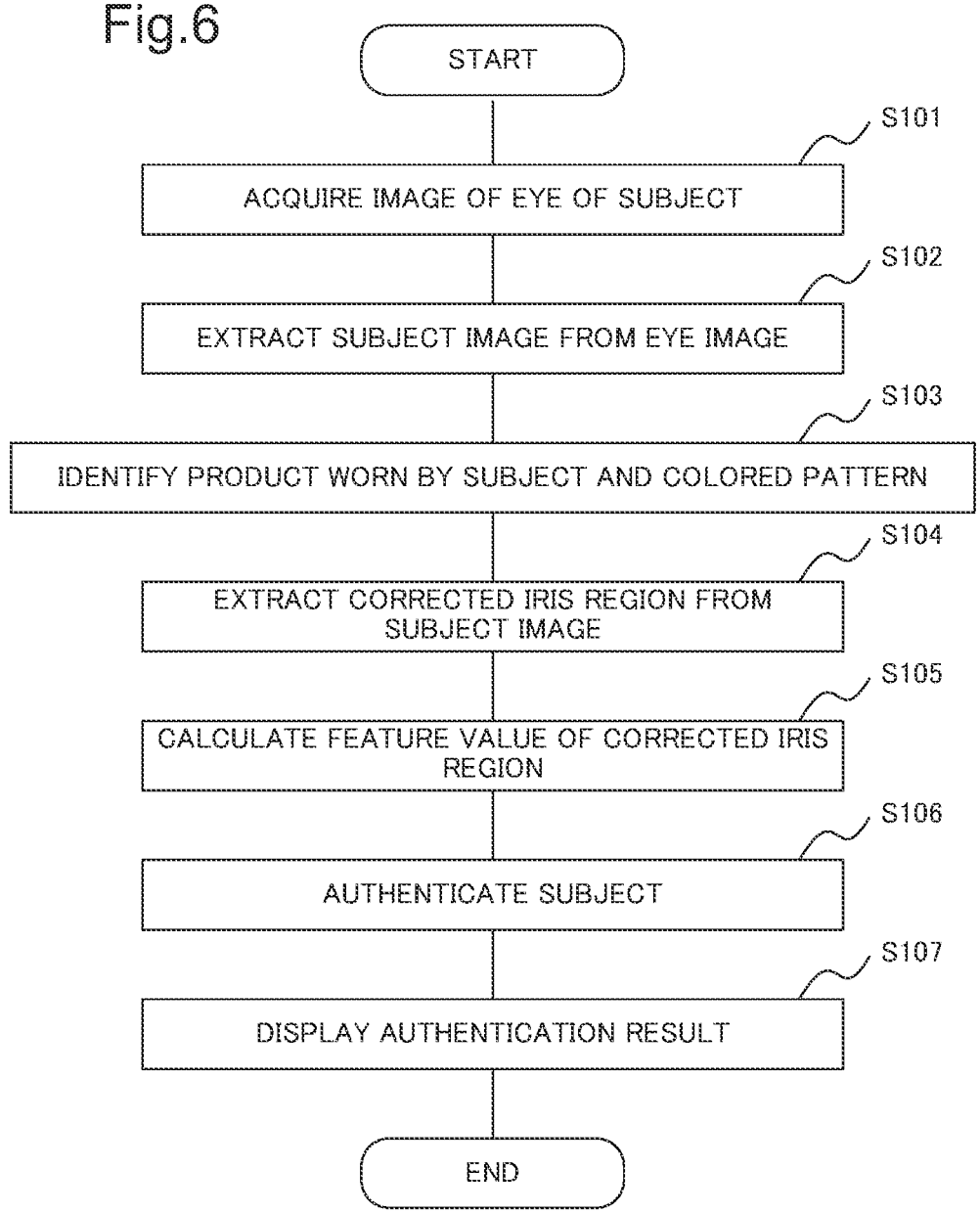
FIG. 6 is a flowchart showing an authentication process in the authentication device 11 according to the first example embodiment.
Figure 7:
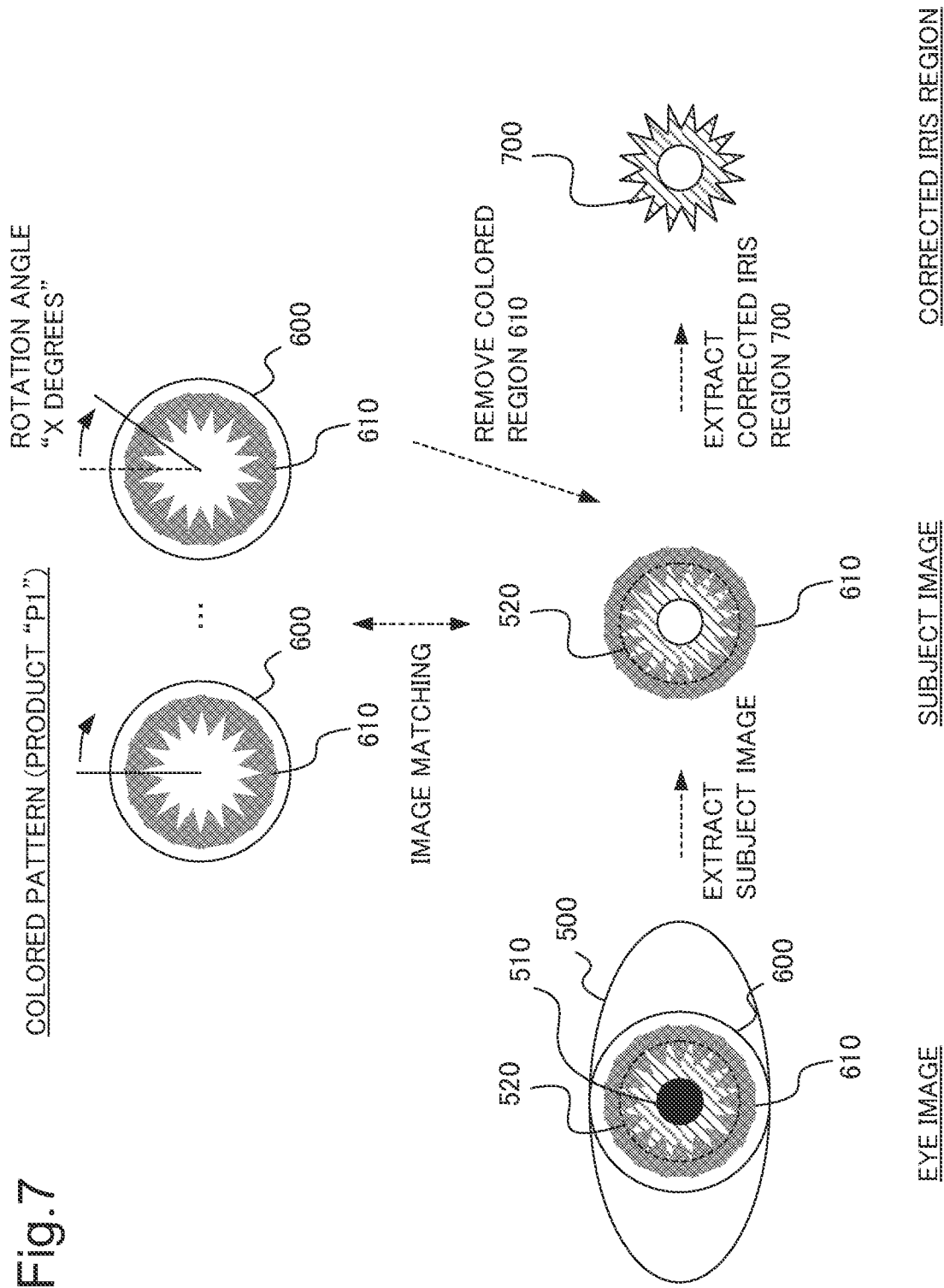
FIG. 7 is a diagram showing an example of extraction of a corrected iris region 700 according to the first example embodiment.

FIG. 6 is a flowchart showing an authentication process in the authentication device 11 according to the first example embodiment. FIG. 7 is a diagram showing an example of extraction of the corrected iris region 700 according to the first example embodiment.

First, the image acquisition unit 111 acquires an image of an eye 500 of a subject (step S101).

For example, the image acquisition unit 111 acquires an image of an eye 500 (right eye) on which a colored contact lens 600 is worn as shown in FIG. 7.

The identification unit 121 extracts an iris-like region from the image of the eye 500 acquired in step S101 as an image to be processed (hereinafter also referred to as a subject image) (step S102). The "iris-like region" is a combined region of the region of an iris 520 and a colored region 610 when the colored contact lens 600 is being worn, or is the region of the iris 520 when the colored contact lens 600 is not being worn.

For example, the identification unit 121 extracts the subject image from the image of the eye 500 as shown in FIG. 7.

The identification unit 121 compares the colored patterns of the products included in the product information 211 with the subject image extracted in step S102, to identify the product worn by the subject. The identification unit 121 identifies the colored pattern of the identified product as the colored pattern of the colored contact lens 600 being worn by the subject (step S103). Here, the identification unit 121 performs image matching between the colored patterns and the subject image while rotating the colored pattern of each product, to identify a product and a rotation angle with a high matching degree.

For example, the identification unit 121 calculates a matching degree at each rotation angle while rotating the colored pattern of each product included in the product information 211 in FIG. 3 by a predetermined angle at a time in a predetermined rotation direction around a position associated to the center of the pupil 510. The identification unit 121 identifies a product "P1" and a rotation angle "X degrees" with the largest matching degree equal to or more than a predetermined value as shown in FIG. 7.

As a method of the image matching, any method may be used as long as a matching degree between two images can be obtained. For example, as a matching degree, the sum total of differences between associated pixels, the number of pixels with the number of differences between the pixels being equal to or less than a threshold value, or a correlation coefficient between images may be calculated. For a product that does not rotate when worn such as an astigmatic contact lens, or a product whose colored pattern does not change when rotated, the identification of a rotation angle may be omitted.

The extraction unit 131 extracts a corrected iris region 700 of the subject from the subject image (step S104). Here, the extraction unit 131 superimposes the colored pattern identified in step S103 on the subject image at the identified angle. Then, the extraction unit 131 extracts, as the corrected iris region 700, a region obtained by removing the colored region 610 of the identified colored pattern from the subject image.

For example, as shown in FIG. 7, the extraction unit 131 removes the colored region 610 of the identified product "P1" from the subject image, to extract the corrected iris region 700.

The extraction unit 131 may alternatively determine a maximum radius of the identified colored pattern not including the colored region 610 around a position associated to the center of the pupil 510. Then, the extraction unit 131 may extract, as the corrected iris region 700, a region obtained by removing the outside of a circle of the determined radius from the subject image.

Figure 8:
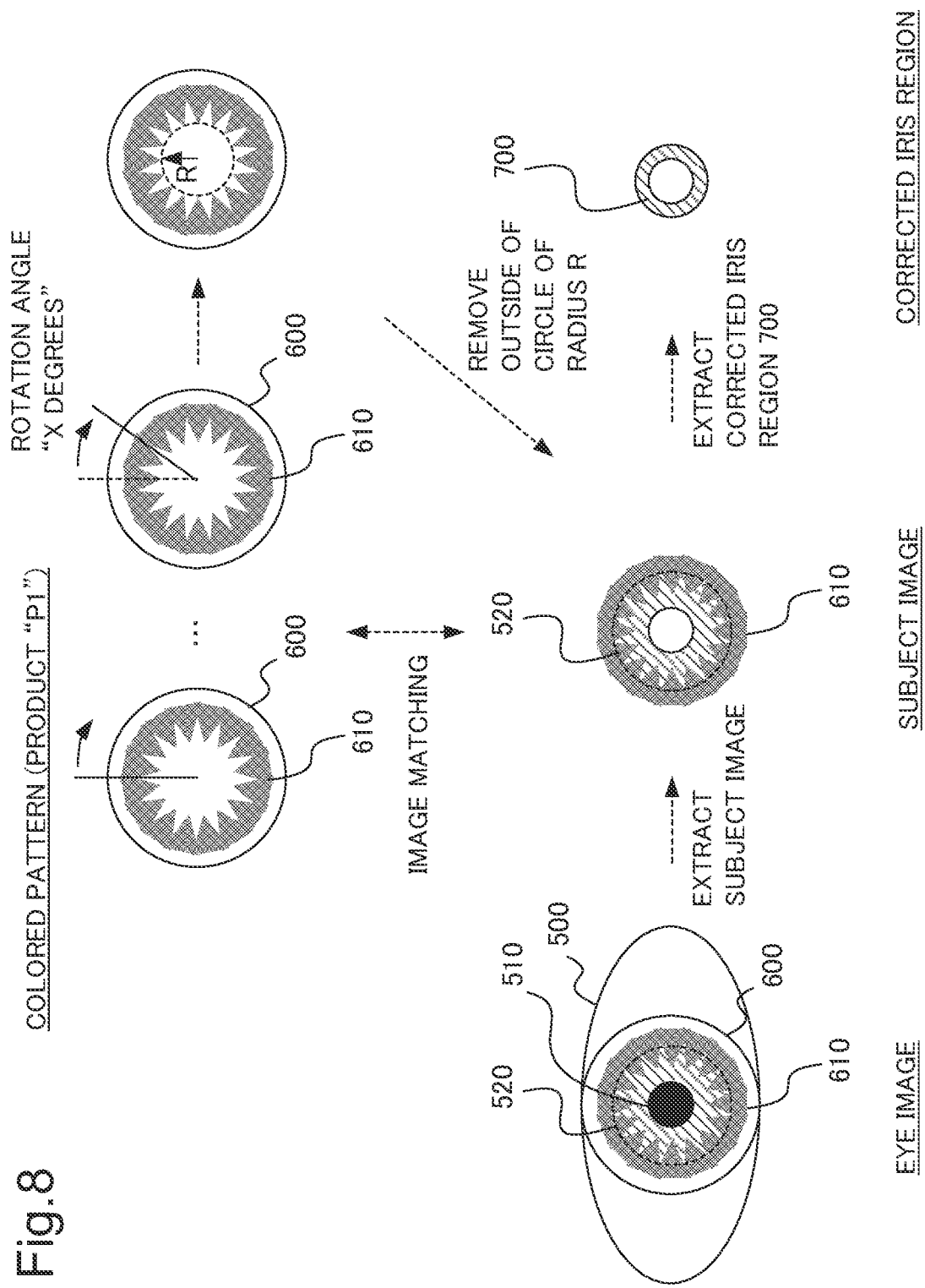
FIG. 8 is a diagram showing another example of extraction of the corrected iris region 700 according to the first example embodiment.

FIG. 8 is a diagram showing another example of extraction of the corrected iris region 700 according to the first example embodiment.

In this case, for example, as shown in FIG. 8, the extraction unit 131 determines a maximum radius "R" not including the colored region 610 from the colored pattern of the identified product "P1". Then, the extraction unit 131 extracts the corrected iris region 700 by removing the outside of a circle of the radius "R" from the subject image.

The feature value calculation unit 141 calculates the feature value of the corrected iris region 700 extracted in step S104 (step S105). Here, as the feature value, the feature value calculation unit 141 uses, for example, a bit string obtained by encoding an image of the corrected iris region 700 with a predetermined algorithm.

For example, the feature value calculation unit 141 calculates a feature value "FRt" of the corrected iris region 700 shown in FIG. 7.

The authentication unit 151 matches the feature value of the corrected iris region 700 of the subject calculated in step S105 against the feature values of the individuals' iris regions included in the authentication information 221, to authenticate the subject (step S106). Here, the authentication unit 151 matches the feature value of the corrected iris region 700 of the subject against the feature values of the individuals' iris regions on the eye 500 (right eye or left eye) corresponding to the subject image.

For example, the authentication unit 151 matches the feature value "FRt" of the corrected iris region 700 against the feature values "FRj" of the individuals' iris regions in the authentication information 221 in FIG. 4, and identifies the subject as an individual "U1".

The display unit 161 displays the authentication result (step S107). Here, when an individual can be identified in step S106, the display unit 161 may display authentication success or the individual identifier of the identified subject as the authentication result. If an individual cannot be identified in step S106, the display unit 161 may display authentication failure as the authentication result.

Figure 9:
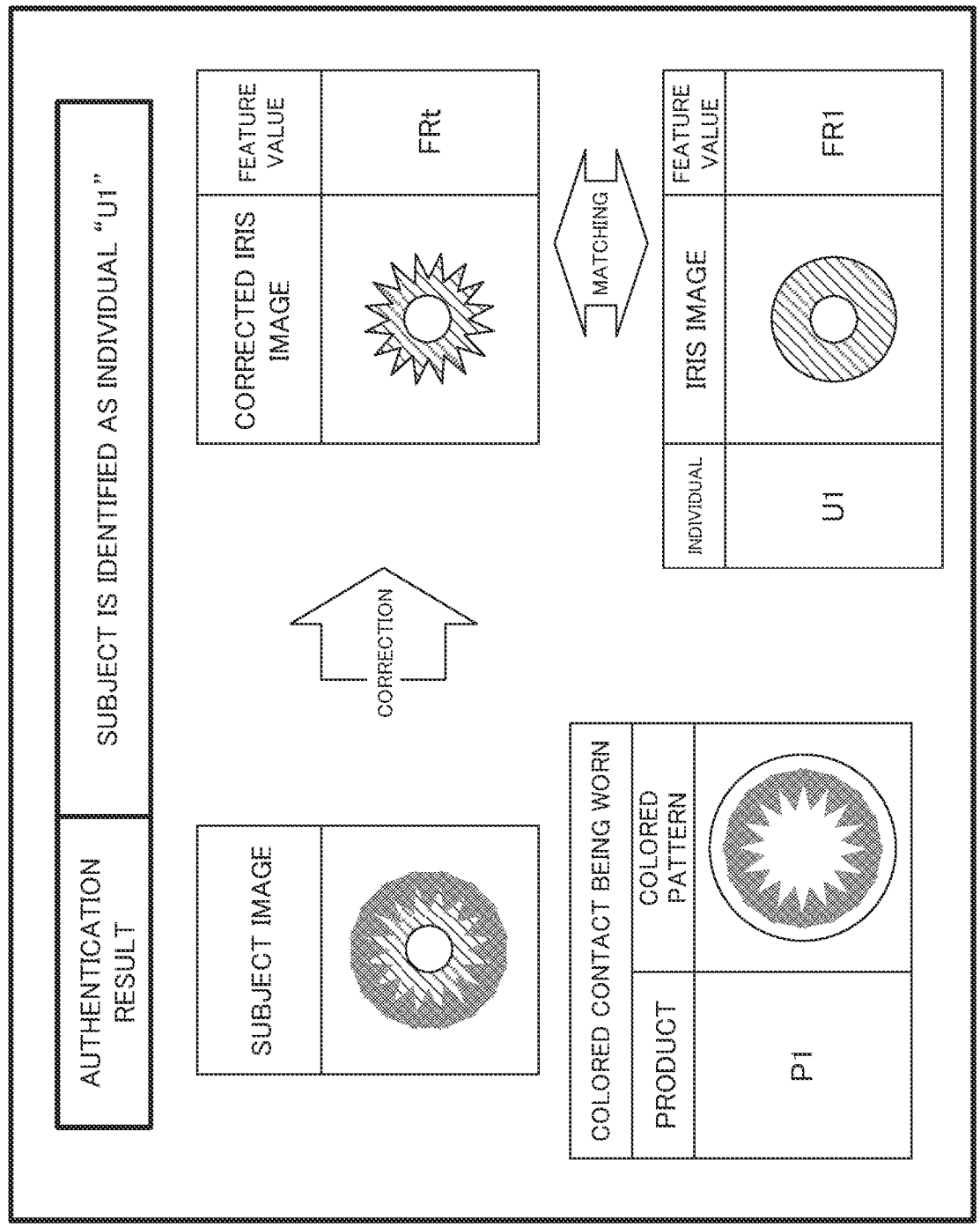
FIG. 9 is a diagram showing an example of a screen showing an authentication result according to the first example embodiment.

FIG. 9 is a diagram showing an example of a screen showing an authentication result according to the first example embodiment. The screen in FIG. 9 shows that, as the matching result, the subject is identified as the individual "U1". In addition to the authentication result, the subject image, the identified product "P1" and colored pattern, the image (corrected iris image) and the feature value of the corrected iris region 700, and the iris image and the feature value of the identified individual are shown.

For example, the display unit 161 displays the screen in FIG. 9 as the authentication result.

Thus, the operation of the authentication device 11 according to the first example embodiment is completed.

If a colored pattern cannot be identified in step S103 described above, the identification unit 121 may determine that the colored contact lens 600 is not being worn on the eye 500 of the subject. In this case, the feature value calculation unit 141 calculates the feature value of the region of the iris 520 in the subject image, instead of the feature value of the corrected iris region 700, and the authentication unit 151 authenticates the subject using the feature value.

In step S106 described above, the authentication unit 151 may use, as the individuals' feature values to be matched against the feature value of the subject, feature values of the individuals' corrected iris regions that have been calculated on the assumption that the individuals wear the identified product. In this case, the authentication unit 151 extracts a corrected iris region from each individual's iris region included in the authentication information 221, using the identified colored pattern in the same manner as in step S104, for example, to calculate the feature value of the corrected iris region.

For example, the authentication unit 151 removes the colored region 610 of the colored pattern of the identified product identifier "P1" from each individual's iris region to extract a corrected iris region. The authentication unit 151 calculates a feature value "FR'j" of the corrected iris region of each individual. The authentication unit 151 matches the feature value "FRt" of the corrected iris region 700 of the subject against the feature value "FR'j" of the corrected iris region of each individual.

Next, a characteristic configuration of the first example embodiment will be described.

Figure 10:
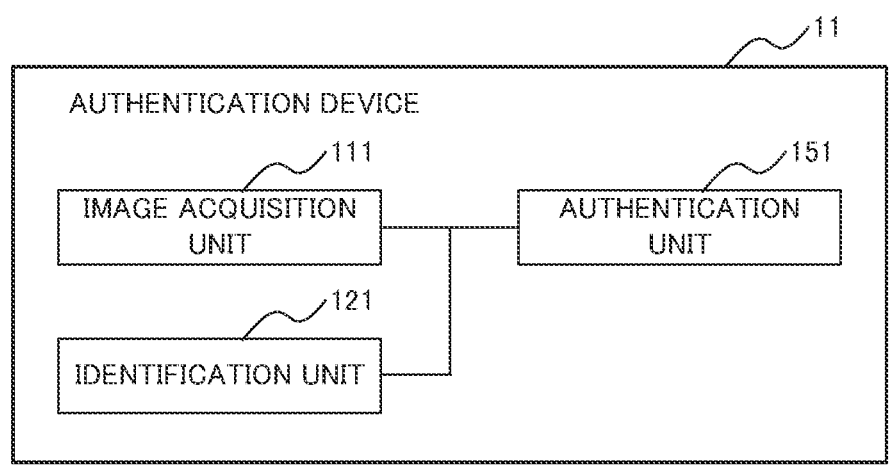
FIG. 10 is a functional block diagram of a characteristic configuration in the first example embodiment.

FIG. 10 is a functional block diagram of a characteristic configuration of the first example embodiment.

The authentication device 11 includes the image acquisition unit 111, the identification unit 121, and the authentication unit 151. The image acquisition unit 111 acquires an image of an eye of a subject. The identification unit 121 compares reference images with the image of the eye, to identify the colored pattern of a colored contact lens worn by the subject. The authentication unit 151 identifies the subject using a feature in a region other than a colored region of the colored pattern in the iris region of the eye.

Next, the effect of the first example embodiment will be described.

According to the first example embodiment, even when a colored contact lens is worn, a reduction in the authentication precision of iris authentication can be prevented. The reason is that the authentication device 11 identifies the colored pattern of a colored contact lens worn by a subject by comparing reference images with an image of an eye, and identifies the subject using a feature in a region other than a colored region of the colored pattern in the iris region of the eye.

According to the first example embodiment, a colored contact lens product being worn can be identified. The reason is that the authentication device 11 identifies a product being worn by a subject from a plurality of products by comparing the colored pattern of each of the plurality of products with an image of an eye of the subject. Thus, a colored contact lens product can be presented, for example, as information indicating one of articles being worn by a subject.

Second Example Embodiment

Next, a second example embodiment will be described. The second example embodiment is different from the first example embodiment in that an image of one eye 500 of both eyes 500 of a subject is used as a reference image.

First, a configuration of an authentication system 2 according to the second example embodiment will be described.

Figure 11:
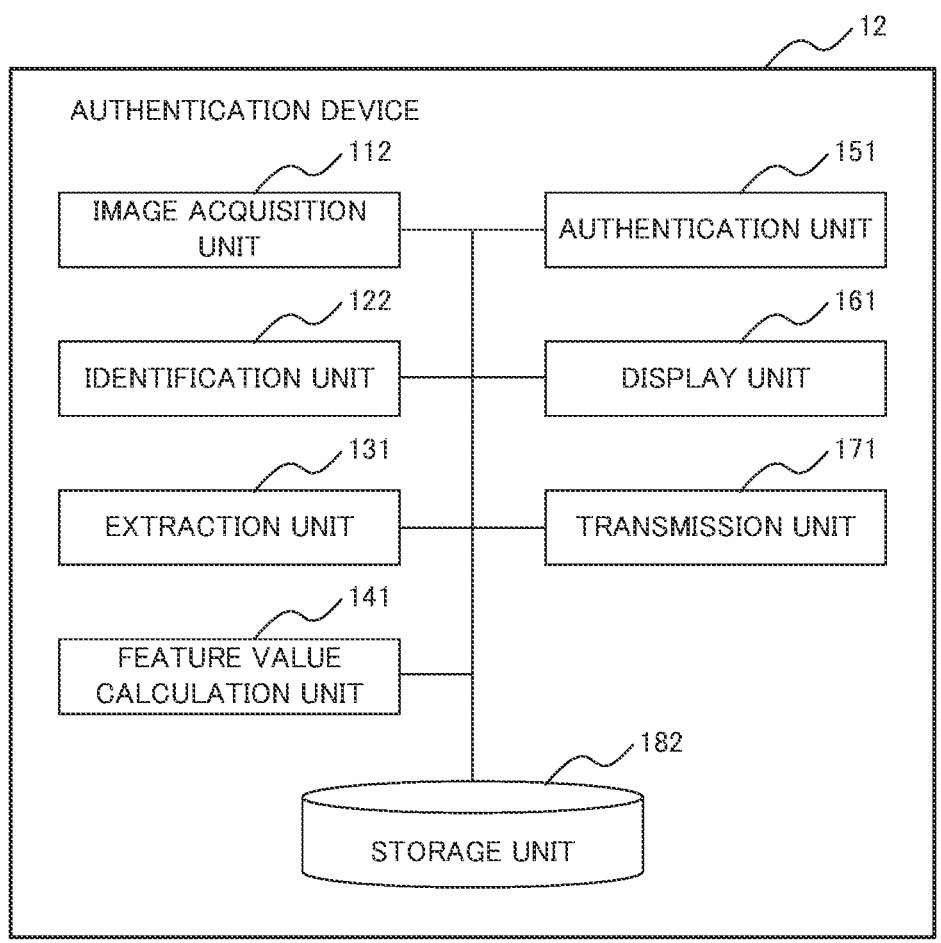
FIG. 11 is a functional block diagram of an authentication system 2 according to a second example embodiment.

FIG. 11 is a functional block diagram of the authentication system 2 according to the second example embodiment. The authentication system 2 includes an authentication device 12. In the authentication device 12 according to the second example embodiment, the image acquisition unit 111, the identification unit 121, and the storage unit 181 in the authentication device 11 according to the first example embodiment are replaced by an image acquisition unit 112, an identification unit 122, and a storage unit 182, respectively.

The image acquisition unit 112 acquires images of both eyes 500 of a subject.

The identification unit 122 compares the image of one eye 500 of both eyes 500 of the subject (reference image) with the image of the other eye 500, to identify the colored pattern of colored contact lenses 600 worn by the subject. Generally, the colored contact lenses 600 of the same colored pattern are worn on both eyes 500. On the other hand, the patterns of the irises 520 of the right and left eyes 500 are different from each other. Therefore, by comparing the images of both eyes 500 on which the colored contact lenses 600 are worn, the colored pattern can be identified.

The storage unit 182 stores the authentication information 221.

Next, the operation of the authentication device 12 according to the second example embodiment will be described.

Here, it is assumed that the storage unit 182 stores the authentication information 221 in FIG. 4.

Figure 12:
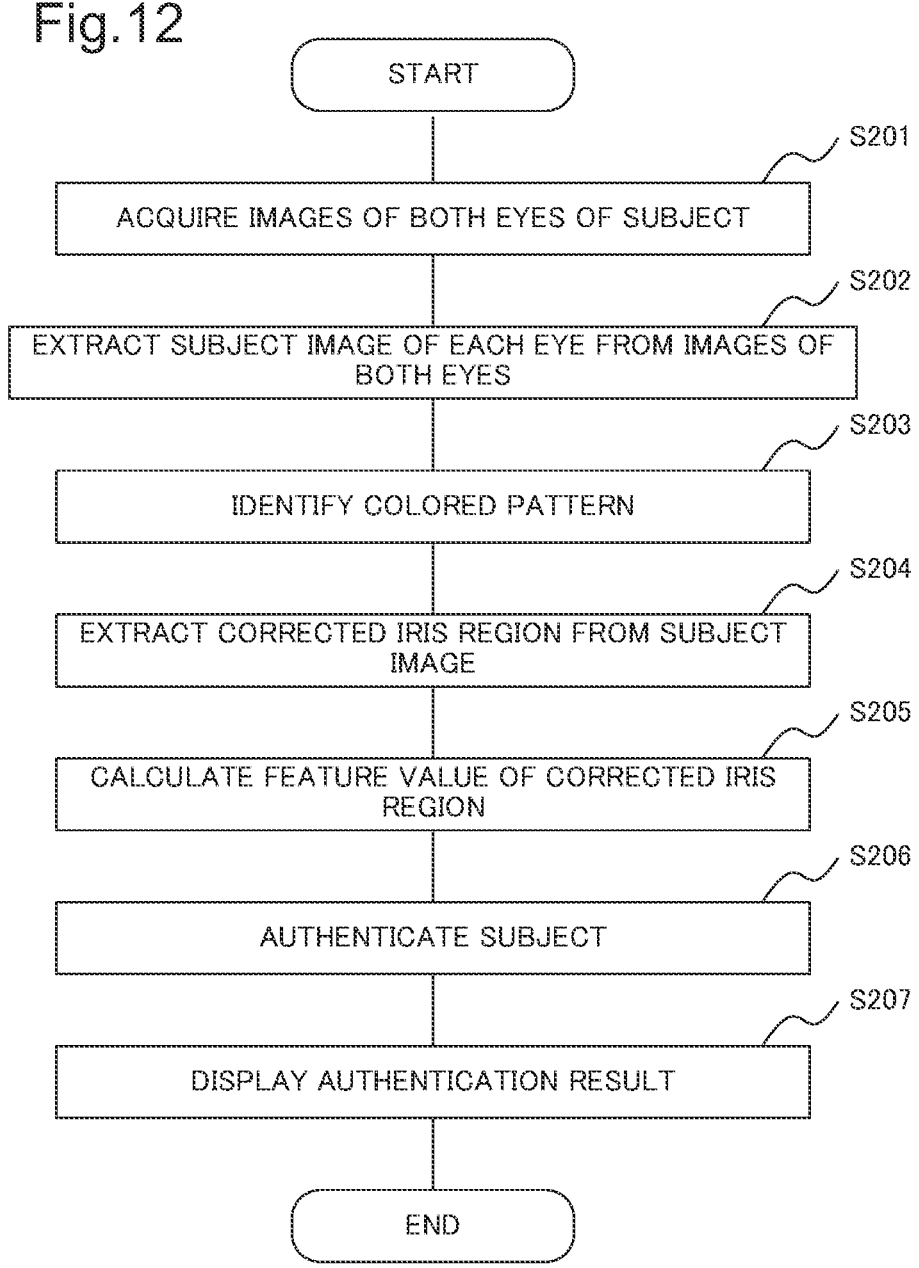
FIG. 12 is a flowchart showing an authentication process in an authentication device 13 according to the second example embodiment.
Figure 13:
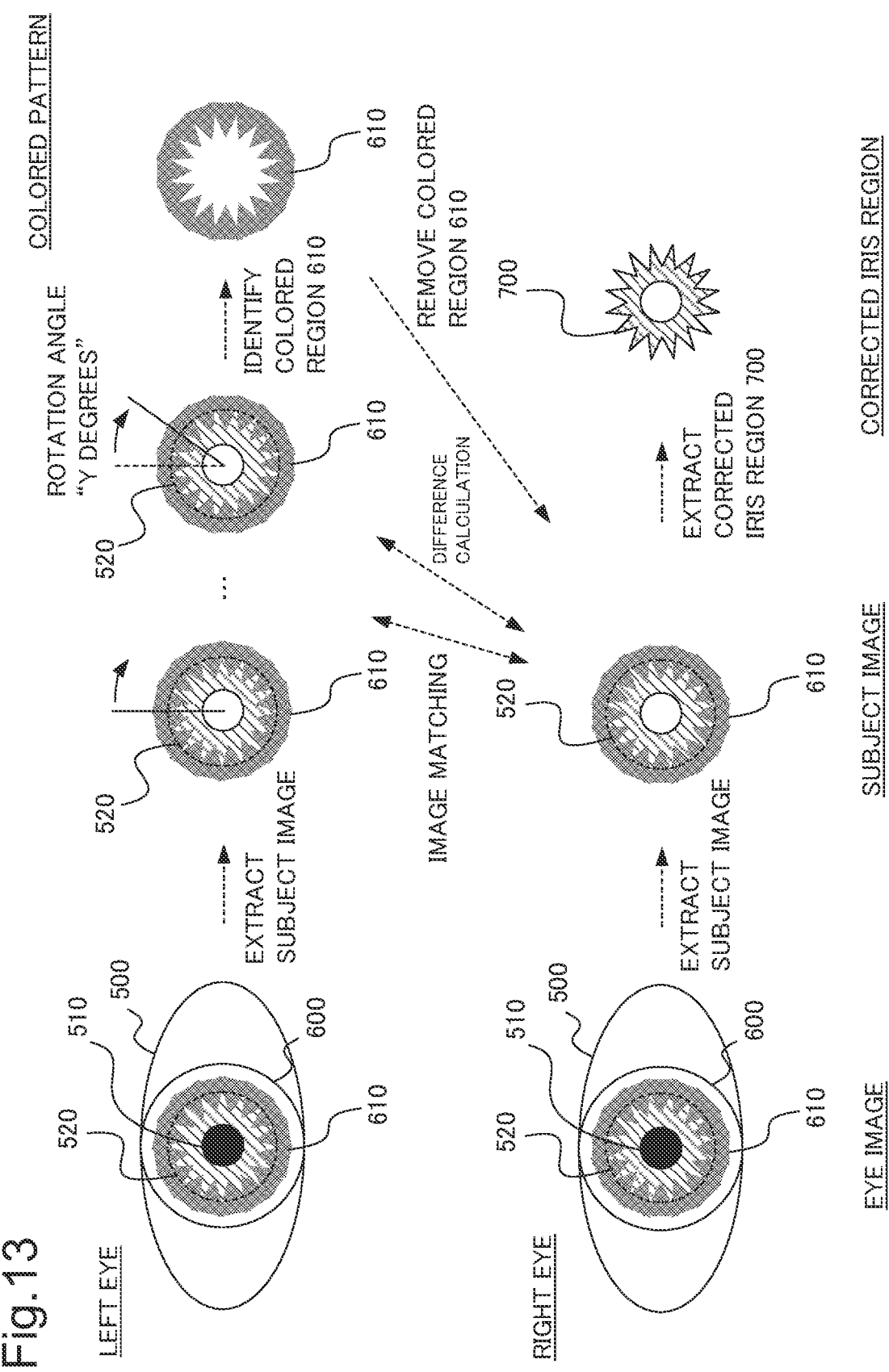
FIG. 13 is a diagram showing an example of extraction of a corrected iris region 700 according to the second example embodiment.

FIG. 12 is a flowchart showing an authentication process in the authentication device 12 according to the second example embodiment. FIG. 13 is a diagram showing an example of extraction of a corrected iris region 700 according to the second example embodiment.

First, the image acquisition unit 112 acquires images of both eyes 500 of a subject (step S201).

For example, the image acquisition unit 112 acquires images of both eyes 500 (the right eye and the left eye) on which colored contact lenses 600 are being worn as shown in FIG. 13.

The identification unit 122 extracts a subject image of each eye 500 from the images of both eyes 500 acquired in step S201 (step S202).

For example, as shown in FIG. 13, the identification unit 122 extracts, from the images of both eyes 500, a subject image of the right eye 500 and a subject image of the left eye 500.

The identification unit 122 compares the subject images of both eyes 500 extracted in step S202, to identify the colored pattern of the colored contact lenses 600 worn by the subject (step S203). Here, the identification unit 122 compares the subject images of both eyes 500 (performs image matching) while rotating the subject image of one eye 500, to identify a rotation angle with a high matching degree. Then, the identification unit 122 identifies a region where the values of associated pixels are similar between the subject images of both eyes 500 when the subject image of one eye 500 is rotated to the identified rotation angle, as the colored region 610 of the colored pattern of the colored contact lenses 600.

For example, the identification unit 122 calculates a matching degree at each rotation angle while rotating the subject image of the left eye 500 by a predetermined angle at a time in a predetermined rotation direction around a position associated to the center of the pupil 510. The identification unit 122 identifies a rotation angle "Y degrees" with the largest matching degree equal to or more than a predetermined value as shown in FIG. 13. The identification unit 122 calculates differences between the values of associated pixels between the subject images of both eyes 500 when the subject image of the left eye 500 is rotated to the identified rotation angle. As shown in FIG. 13, the identification unit 122 identifies a region where the differences are less than a predetermined value as the colored region 610.

In order to prevent a region not covered by the colored region 610 in the region of the iris 520 of the eye 500 from being erroneously identified as the colored region 610, the identification unit 122 may identify the colored region 610 using differences between the values of associated pixels between the subject images as follows. For example, on circles of different radii around a position associated to the center of the pupil 510, the identification unit 122 calculates the number of pixels in which differences in value between the subject images are less than a predetermined value, among the pixels on each circle. The identification unit 122 determines a circle with the calculated number of pixels equal to or more than a threshold value as a circle on the colored region 610. The identification unit 122 determines the minimum radius of the radii of circles determined as circles on the colored region 610. The identification unit 122 identifies the region outside the determined minimum radius as the colored region 610.

The extraction unit 131 extracts a corrected iris region 700 of the subject from the subject image (step S204).

For example, as shown in FIG. 13, the extraction unit 131 removes the colored region 610 of the identified colored pattern from the subject image of the right eye 500, to extract the corrected iris region 700.

Thereafter, as in the first example embodiment, the feature value calculation unit 141 calculates the feature value of the corrected iris region 700 (step S205). Then, the authentication unit 151 authenticates the subject, using the feature value of the corrected iris region 700 (step S206), and the display unit 161 displays the authentication result (step S207).

Thus, the operation of the authentication device 12 according to the second example embodiment is completed.

Next, the effect of the second example embodiment will be described. According to the second example embodiment, a reduction in the authentication precision of iris authentication can be prevented without preparing product colored patterns or the like. The reason is that the authentication device 12 identifies the colored pattern of colored contact lenses by comparing an image of one eye of both eyes of a subject with an image of the other eye.

Third Example Embodiment

Next, a third example embodiment will be described. The third example embodiment is different from the first example embodiment in that, as a feature value of each individual to be matched against in authentication, the feature value of a corrected iris region calculated in advance for each colored contact lens product is used instead of the feature value of an iris region.

First, a configuration of an authentication system 3 according to the third example embodiment will be described.

Figure 14:
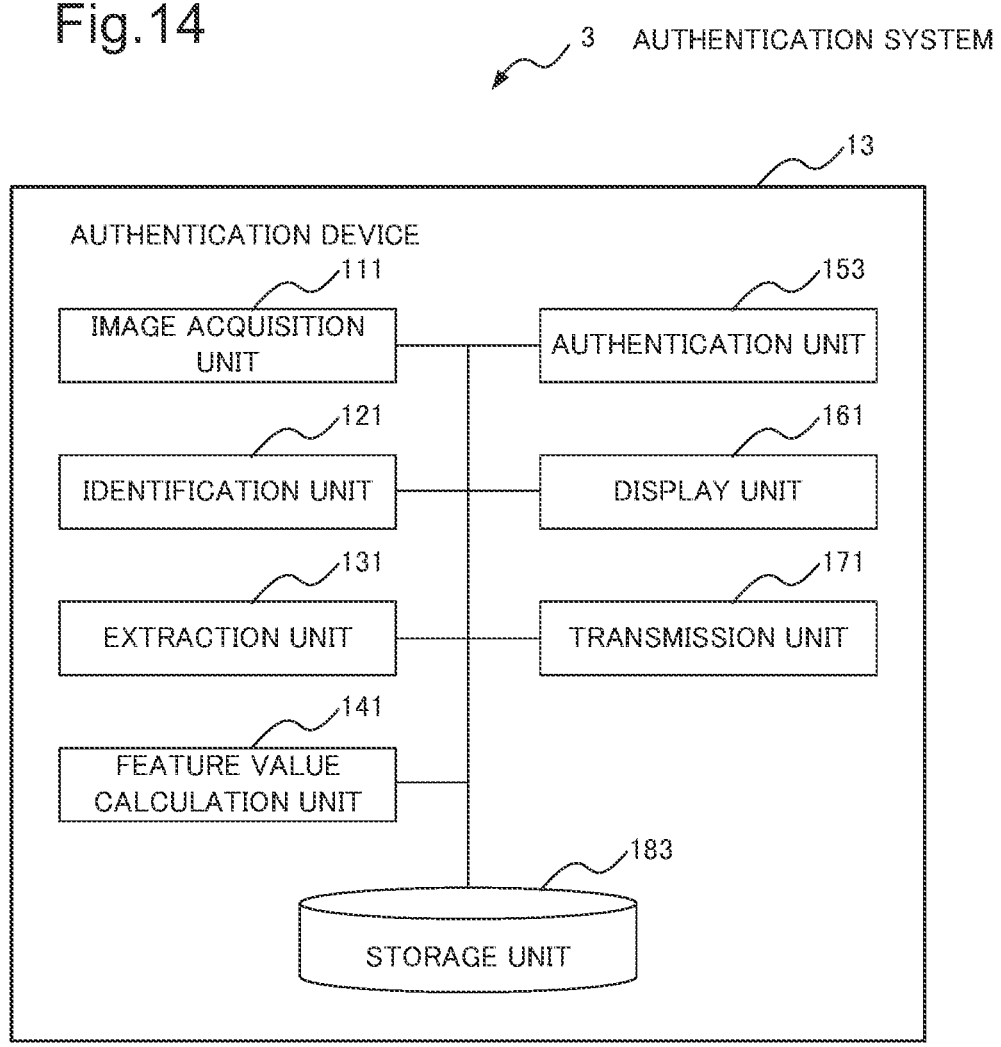
FIG. 14 is a functional block diagram of an authentication system 3 according to a third example embodiment.

FIG. 14 is a functional block diagram of the authentication system 3 according to the third example embodiment. The authentication system 3 includes an authentication device 13. In the authentication device 13 according to the third example embodiment, the authentication unit 151 and the storage unit 181 in the authentication device 11 according to the first example embodiment are replaced by an authentication unit 153 and a storage unit 183, respectively.

The authentication unit 153 matches the feature value of a corrected iris region of a subject against the feature value of a corrected iris region of each individual associated with an identified product, to authenticate the subject. The feature value of a corrected iris region of each individual for each product is calculated in advance by an administrator or the like on the assumption that the individual wears the product, and is set in authentication information 223. In this case, a corrected iris region is extracted from each individual's iris region, using the colored pattern of each product in the same manner as in step S104, for example, and the feature value of the corrected iris region is calculated.

FIG. 15 is a diagram showing an example of the authentication information 223 according to the third example embodiment. The authentication information 223 in FIG. 15 includes individual identifiers "Uj", and product identifiers "Pi" and feature values "FR'ji" and "FL'ji" calculated for corrected iris regions of both eyes 500 of the individuals, which are associated with the individual identifiers.

The storage unit 183 stores the product information 211 and the authentication information 223.

Next, the operation of the authentication device 13 according to the third example embodiment will be described.

Here, it is assumed that the storage unit 183 stores the product information 211 in FIG. 3 and the authentication information 223 in FIG. 15.

A flowchart showing an authentication process in the authentication device 11 according to the third example embodiment is the same as that of the first example embodiment (FIG. 6) except for the processing in step S106.

In step S106, the authentication unit 153 matches the feature value of the corrected iris region 700 of the subject calculated in step S105 against the feature values of the corrected iris regions of the individuals associated with the product identified in step S103 included in the authentication information 223, to authenticate the subject.

For example, when the product "P1" is identified, the authentication unit 153 matches the feature value "FRt" of the corrected iris region 700 of the subject against the feature values "FR'j1" of the corrected iris regions of the individuals associated with the product "P1".

In a case where the authentication unit 153 performs authentication using a determination device created by machine learning, a determination device associated with each product may be created using the feature values of corrected iris regions of individuals for the product as learning data.

Thus, the operation of the authentication device 13 according to the third example embodiment is completed.

Next, the effect of the third example embodiment will be described.

According to the third example embodiment, the authentication precision of iris authentication when a colored contact lens is worn can be improved, compared to the first example embodiment. The reason is that the authentication device 13 matches the feature value of a corrected iris region of a subject against feature values of corrected iris regions of individuals associated with an identified product, to authenticate the subject.

Fourth Example Embodiment

Next, a fourth example embodiment will be described. The fourth example embodiment is different from the first example embodiment in that an identified colored contact lens product is used to narrow down individuals to be matched against in an authentication process.

First, a configuration of an authentication system 4 according to the fourth example embodiment will be described.

Figure 16:
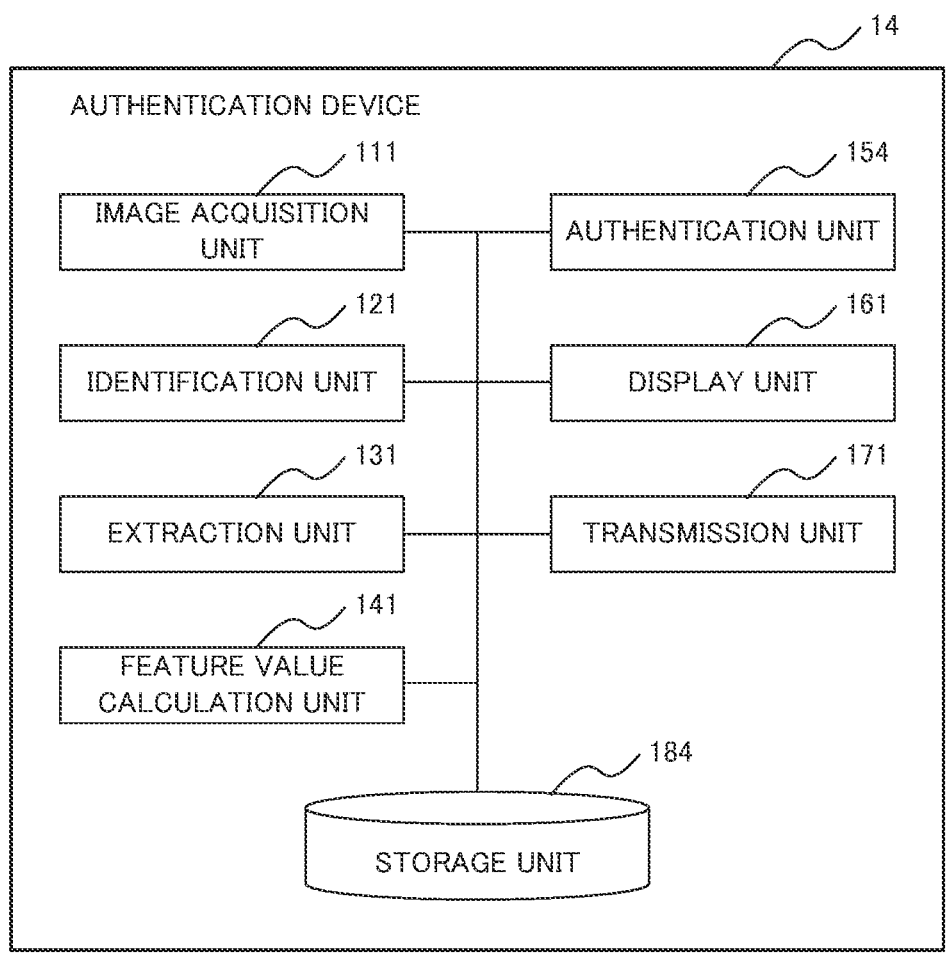
FIG. 16 is a functional block diagram of an authentication system 4 according to a fourth example embodiment.

FIG. 16 is a functional block diagram of the authentication system 4 according to the fourth example embodiment. The authentication system 4 includes an authentication device 14. In the authentication device 14 according to the fourth example embodiment, the authentication unit 151 and the storage unit 181 in the authentication device 11 according to the first example embodiment are replaced by an authentication unit 154 and a storage unit 184, respectively.

When an individual is identified as a subject by the authentication process, the authentication unit 154 associates a product identified by the identification unit 121 with the identified individual (an individual who has worn the product) and stores them as wearing information 231. Further, in the authentication process after that, the authentication unit 154 refers to the wearing information 231 to narrow down individuals to be matched against to individuals associated with a product identified by the identification unit 121.

FIG. 17 is a diagram showing an example of the wearing information 231 according to the fourth example embodiment. The wearing information 231 in FIG. 17 includes the product identifier "Pi" of each product associated with the individual identifiers "Uj" of individuals who have worn the product.

The storage unit 184 stores the product information 211, the authentication information 221, and the wearing information 231.

Next, the operation of the authentication device 14 according to the fourth example embodiment will be described.

Here, it is assumed that the storage unit 184 stores the product information 211 in FIG. 3 and the authentication information 221 in FIG. 4.

Figure 18:
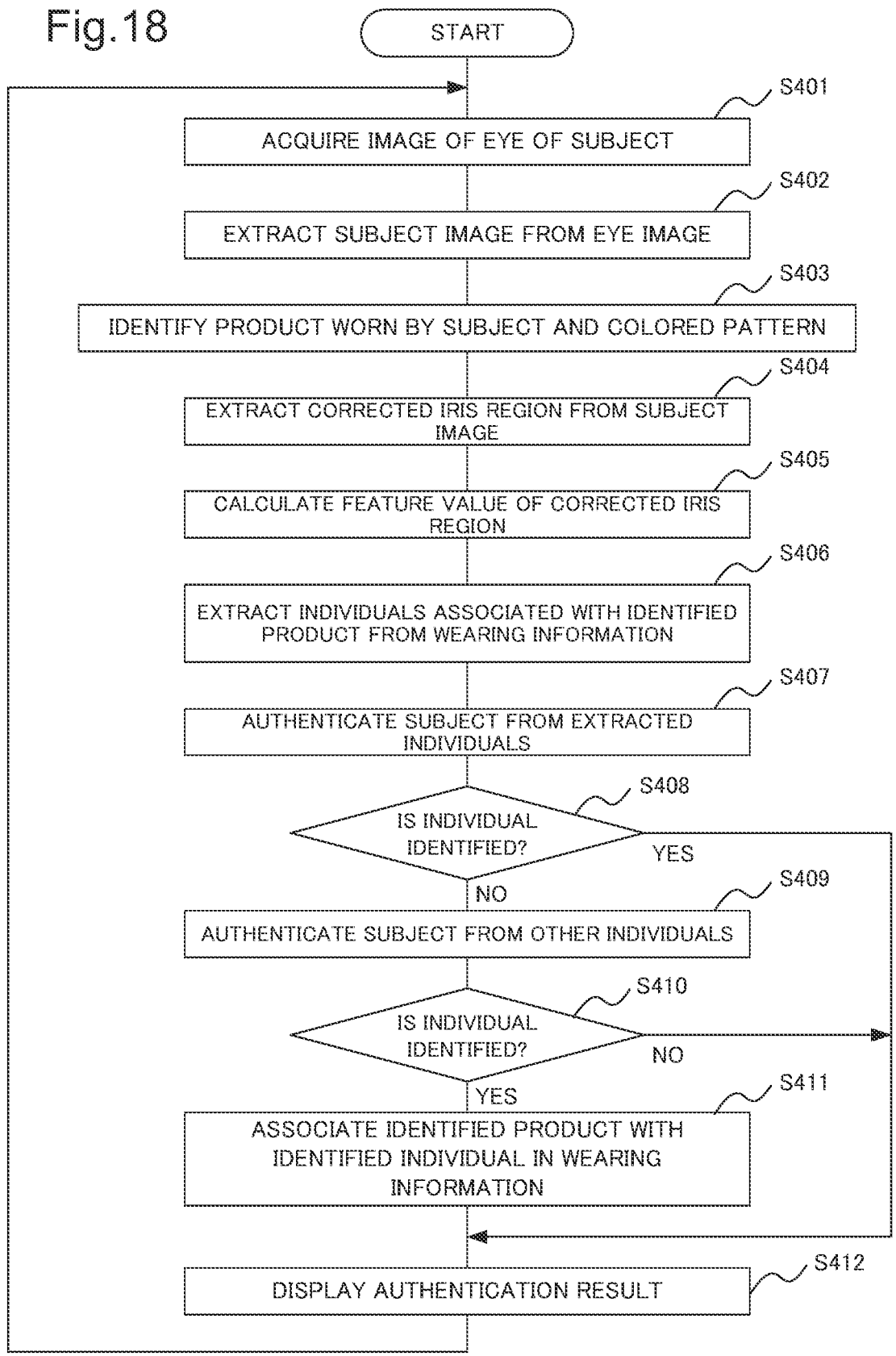
FIG. 18 is a flowchart showing an authentication process in an authentication device 11 according to the fourth example embodiment.

FIG. 18 is a flowchart showing the authentication process in the authentication device 11 according to the fourth example embodiment.

Here, processing in steps S401 to S405 is the same as the processing in steps S101 to S105 of the first example embodiment.

The authentication unit 154 refers to the wearing information 231 to extract individuals associated with the product identified in step S403 (step S406).

The authentication unit 154 matches the feature value of the corrected iris region 700 of the subject calculated in step S405 against the feature values of the iris regions of the individuals extracted in step S406 among the individuals included in the authentication information 221, to authenticate the subject (step S407).

When an individual can be identified in step S407 (step S408/YES), the display unit 161 displays, as the authentication result, authentication success or the individual identifier of the identified subject (step S412).

When an individual cannot be identified in step S407 (step S408/NO), the authentication unit 154 matches the feature value of the corrected iris region 700 of the subject against the feature values of the iris regions of individuals other than the individuals extracted in step S406 among the individuals included in the authentication information 221, to authenticate the subject (step S409).

When an individual can be identified in step S409 (step S410/YES), the authentication unit 154 associates the product identifier of the product identified in step S403 with the individual identifier of the individual identified by the authentication in the wearing information 231 (step S411).

The display unit 161 displays, as the authentication result, authentication success or the individual identifier of the identified subject (step S412).

If an individual cannot be identified in step S409 (step S410/NO), the display unit 161 displays authentication failure as the authentication result (step S412).

Thereafter, the process from step S401 is repeated.

For example, assume that in the authentication process on a certain subject with no individual identifiers being associated with a product "P1" in the wearing information 231, the product "P1" is identified by the identification unit 121, and an individual "U1" by the authentication unit 154. In this case, as shown in FIG. 17, the authentication unit 154 associates the individual "U1" with the product "P1" in the wearing information 231. Further, assume that in the authentication process on another subject, the product "P1" and the individual "U1" are identified. In this case, as shown in FIG. 17, the authentication unit 154 associates an individual "U3" with the product "P1" in the wearing information 231.

Assume that in the process on the same subject or another subject after that, the product "P1" is identified by the identification unit 121. In this case, the authentication unit 154 extracts, from the wearing information 231 in FIG. 17, the individuals "U1", "U3", . . . associated with the product "P1". The authentication unit 154 matches the feature value of the corrected iris region 700 of the subject against the feature values of the iris regions of the extracted individuals "U1", "U3", . . . .

Thus, the operation of the authentication device 14 according to the fourth example embodiment is completed.

According to the fourth example embodiment, the authentication process can be performed in a shorter time than in the first example embodiment. The reason is that the authentication device 14 stores the identifiers of products associated with the identifiers of individuals who have worn the products, and narrows individuals to be matched against to individuals associated with an identified product.

Fifth Example Embodiment

Next, a fifth example embodiment will be described. In the fifth example embodiment, the authentication device 11 according to the first example embodiment is used to identify a colored contact lens product worn by a customer in marketing or the like.

First, a configuration of an analysis system 5 according to the fifth example embodiment will be described.

Figure 19:
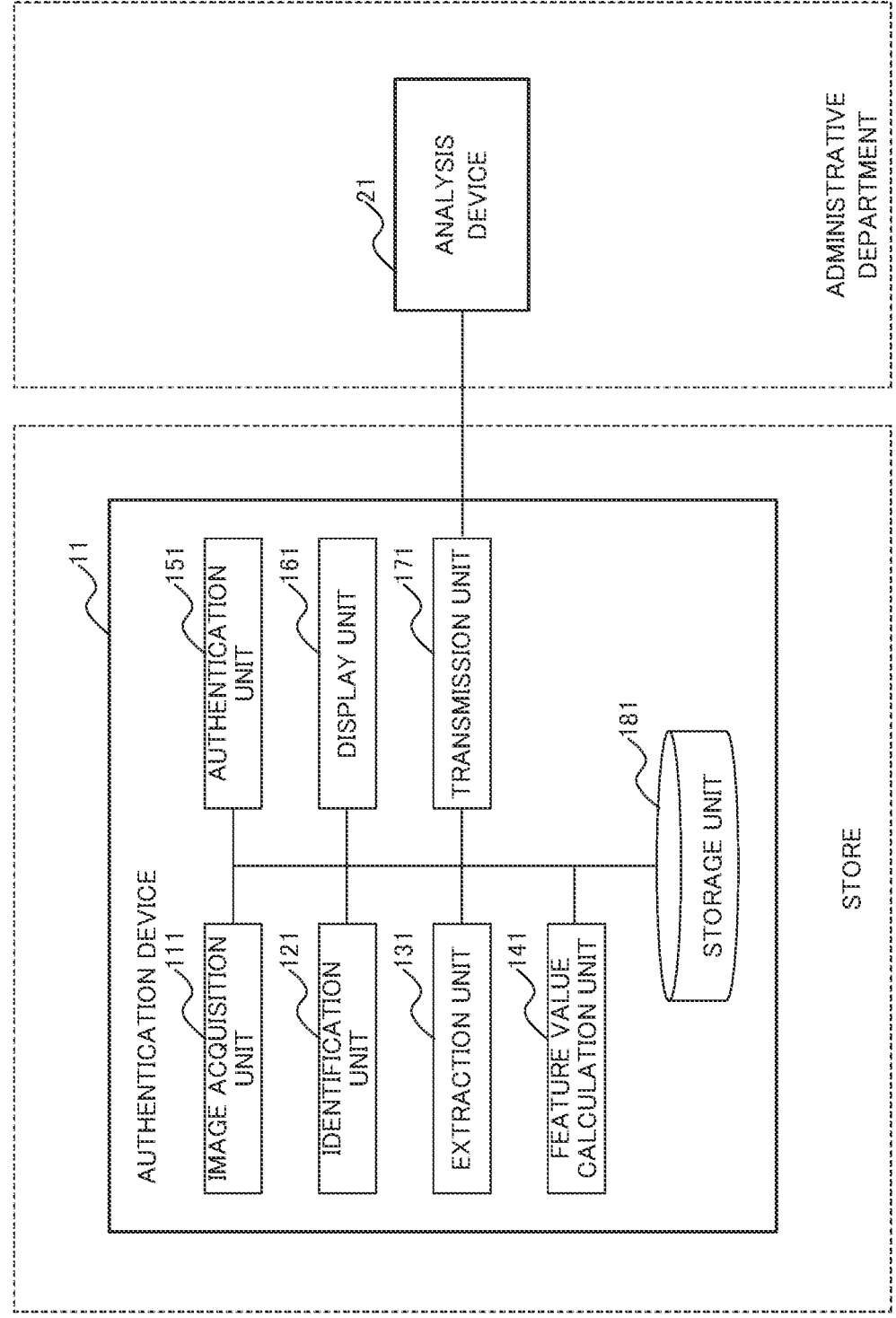
FIG. 19 is a functional block diagram of an analysis system 5 according to a fifth example embodiment.

FIG. 19 is a functional block diagram of the analysis system 5 according to the fifth example embodiment. The analysis system 5 includes an analysis device 21 in addition to the authentication device 11 according to the first example embodiment. The analysis device 21 is, for example, a computer or an information communication terminal having a hardware configuration similar to that of the authentication device 11. The authentication device 11 and the analysis device 21 are connected by a network using wired or wireless communication or the like.

The authentication device 11 is disposed in, for example, stores selling colored contact products, or the like. The analysis device 21 is disposed in, for example, an office or a data center of an administrative department managing the stores. Alternatively, the authentication device 11 and the analysis device 21 may be disposed in the same store.

In a case where a customer visiting the store purchases a commodity, for example, with the customer as a subject, the authentication device 11 identifies a product worn by the subject, and authenticates the subject. The transmission unit 171 of the authentication device 11 transmits a product identifier identified by the identification unit 121 and an individual identifier identified by the authentication unit 151 to the analysis device 21.

The analysis device 21 performs analytical processing on the individual wearing the product, using the product identifier and the individual identifier received from the authentication device 11.

Next, the operation of the analysis system 5 according to the fifth example embodiment will be described.

Figure 20:
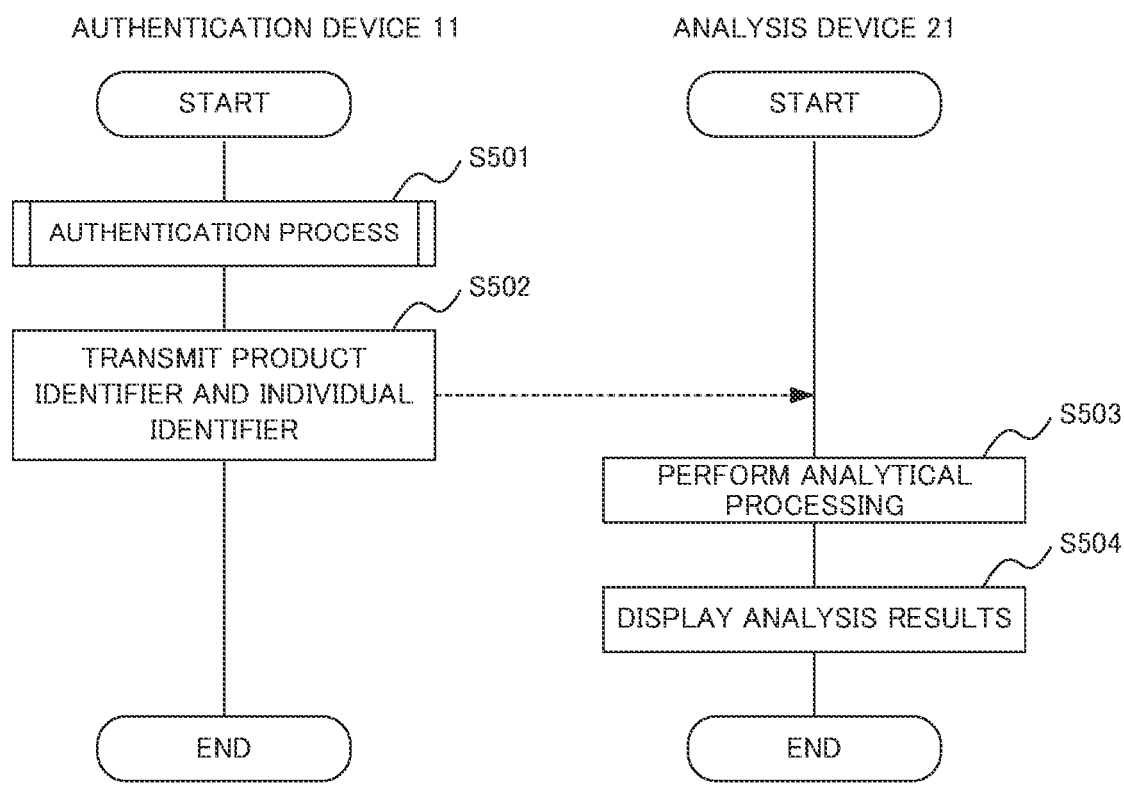
FIG. 20 is a flowchart showing a process in the analysis system 5 according to the fifth example embodiment.

FIG. 20 is a flowchart showing a process in the analysis system 5 according to the fifth example embodiment.

The authentication device 11 authenticates a customer by the same authentication process as in the first example embodiment (FIG. 6) (step S501).

The transmission unit 171 of the authentication device 11 transmits a product identifier and an individual identifier identified in the authentication process to the analysis device 21 (step S502).

The analysis device 21 performs analytical processing using the product identifier and the individual identifier received from the authentication device 11 (step S503).

The analysis device 21 outputs the results of the analytical processing to an administrator or the like (step S504).

The analytical processing is, for example, processing on each product to calculate the total number of individuals wearing the product.

For example, based on product identifiers and individual identifiers received from the authentication device 11 during a predetermined period such as a day, a week, or a month, the analysis device 21 calculates the total number of individuals on each product for each predetermined period and for each store, and outputs them as the analysis results. The output analysis results are used, for example, to determine the number of each product to be purchased to sell at each store, and/or shelf allocation to each product.

The analytical processing may be processing to analyze the relationship between each product and an individual's attribute data. Here, the individual's attribute data may be, for example, data on a commodity purchased by the individual at a store at the time of authentication, commodities or services purchased by the individual in the past, and/or the individual's hobbies and/or preferences. These pieces of data are associated with each individual's individual identifier and stored in a database in a data center or the like. The analysis device 21 acquires, from the data center or the like, data associated with an individual identifier received from the authentication device 11, to perform analytical processing. In addition to an individual's attribute data, various types of data such as the location where the authentication device 11 is installed, the date and time when the authentication process is performed, and the weather when the authentication process is performed may be analyzed for the relationship with each product.

For example, based on product identifiers and individual identifiers received from the authentication device 11 during a predetermined period, the analysis device 21 creates a model on each product which represents the correlation between the product and commodities purchased by the individuals wearing the product. When receiving a product identifier identified for a certain individual from the authentication device 11, the analysis device 21 predicts a commodity having a high correlation with the product, using the created model. The analysis device 21 determines and presents the predicted commodity as a commodity to be recommended to the individual.

Thus, the operation of the analysis system 5 according to the fifth example embodiment is completed.

As the authentication device 11 according to the fifth example embodiment, instead of the authentication device 11 according to the first example embodiment, the authentication device 13 or 14 according to the third or fourth example embodiment may be used.

The analytical processing of the fifth example embodiment may be analytical processing that does not require the identification of individuals. In this case, the analytical processing may be processing to calculate, on each product, the total number of subjects wearing the product. In this case, the analytical processing may be processing to analyze commodities purchased by subjects at a store and the above-described various types of data for the relationship with each product. In this case, instead of the authentication device 11, a device of a configuration in which the extraction unit 131, the feature value calculation unit 141, and the authentication unit 151 are eliminated from the configuration of the authentication device 11 may be used.

Next, the effect of the fifth example embodiment will be described.

According to the fifth example embodiment, various analyses can be performed on individuals wearing colored contact lens products. The reason is that the authentication device 11 transmits identified product identifiers and individual identifiers to the analysis device 21, and the analysis device 21 performs analytical processing using the received product identifiers and individual identifiers.

Sixth Example Embodiment

Next, a sixth example embodiment will be described. In the sixth example embodiment, the authentication device 11 according to the first example embodiment is used to identify a colored contact lens product worn by a subject whose image has been taken by a surveillance camera or the like in a criminal investigation or the like.

First, a configuration of a surveillance system 6 according to the sixth example embodiment will be described.

Figure 21:
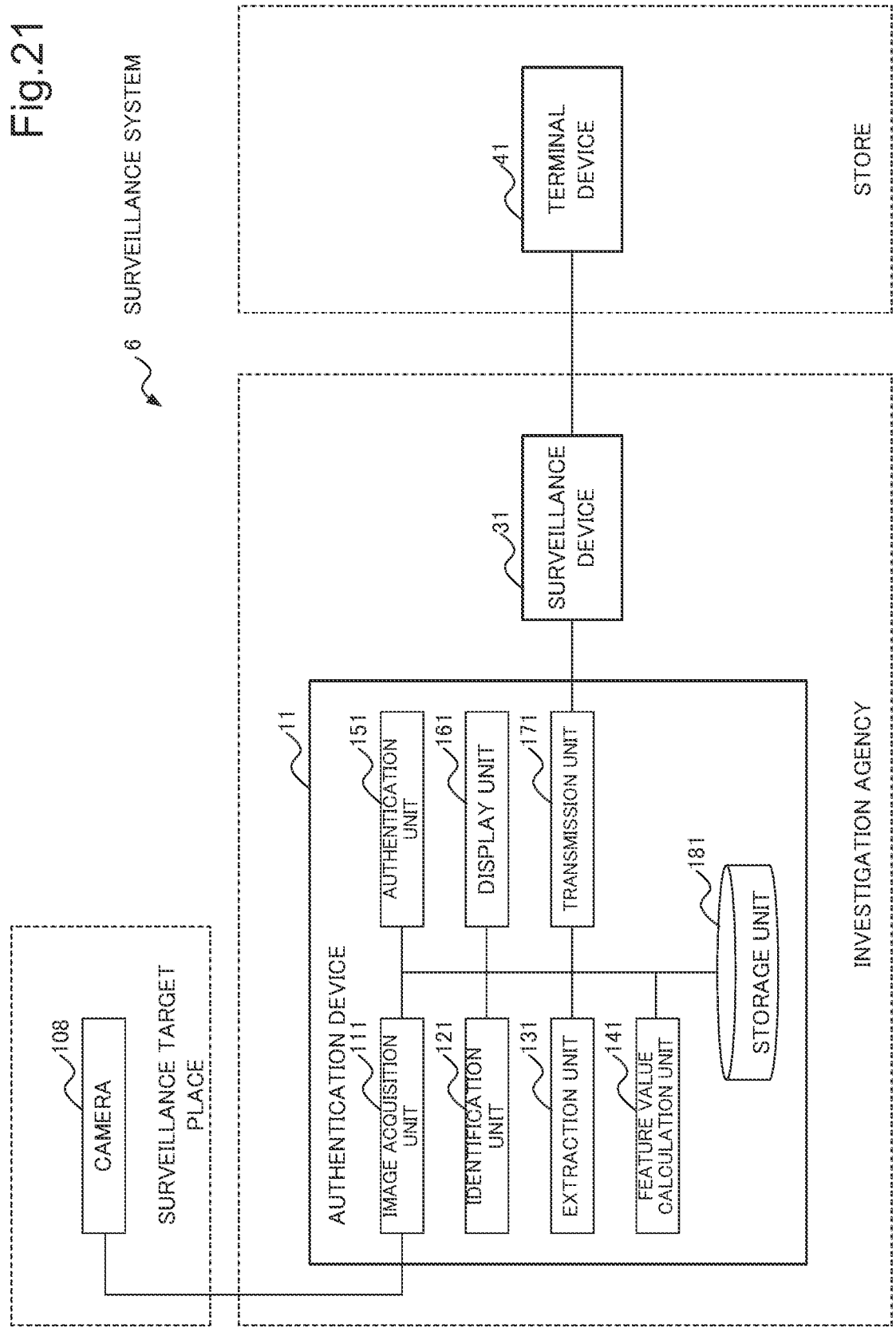
FIG. 21 is a functional block diagram of a surveillance system 6 according to a sixth example embodiment.

FIG. 21 is a functional block diagram of the surveillance system 6 according to the sixth example embodiment. The surveillance system 6 includes, in addition to the authentication device 11 according to the first example embodiment, a surveillance device 31 and a terminal device 41. The surveillance device 31 and the terminal device 41 are, for example, a computer or an information communication terminal having a hardware configuration similar to that of the authentication device 11. The authentication device 11 and the surveillance device 31 are connected by a network using wired or wireless communication or the like. Similarly, the surveillance device 31 and the terminal device 41 are connected by a network using wired or wireless communication or the like.

The camera 108 connected to the authentication device 11 is, for example, a surveillance camera, and is installed at a surveillance target place such as a road, a station, or a shopping center. The authentication device 11 and the surveillance device 31 are installed in, for example, an investigation agency such as the police. The terminal device 41 is installed in, for example, a store selling colored contact lens products.

The authentication device 11 identifies a product being worn by a subject whose image has been taken by the camera 108, and authenticates the subject. The transmission unit 171 of the authentication device 11 transmits a product identifier identified by the identification unit 121 and an individual identifier identified by the authentication unit 151 to the surveillance device 31.

The surveillance device 31 determines whether the individual identifier received from the authentication device 11 is the individual identifier of an individual under surveillance, to detect the individual under surveillance. When the individual under surveillance is detected, the surveillance device 31 displays information about the detected individual to an administrator or the like together with the product identifier received from the authentication device 11. The surveillance device 31 notifies the terminal device 41 that is a notification destination associated with the product, of the information about the detected individual together with the product identifier received from the authentication device 11.

The terminal device 41 displays, to a store clerk or the like, the information about the individual under surveillance received from the surveillance device 31, together with the product identifier received from the authentication device 11.

FIG. 22 is a diagram showing an example of surveillance information 311 according to the sixth example embodiment. The surveillance information 311 in FIG. 22 includes the individual identifiers "Uj" of individuals under surveillance associated with information such as the individuals' names, sexes, and characteristics (heights and weights). FIG. 23 is a diagram showing an example of notification destination information 321 according to the sixth example embodiment. The notification destination information 321 in FIG. 23 includes product identifiers "Pi" associated with the identifiers "Sk" (k is, for example, an integer of one or more) of stores selling the products. The surveillance information 311 and the notification destination information 321 are set in advance in the surveillance device 31 by an administrator or the like.

Next, the operation of the surveillance system 6 according to the sixth example embodiment will be described.

Here, it is assumed that a storage unit of the surveillance device 31 stores the surveillance information 311 in FIG. 22 and the notification destination information 321 in FIG. 23.

Figure 24:
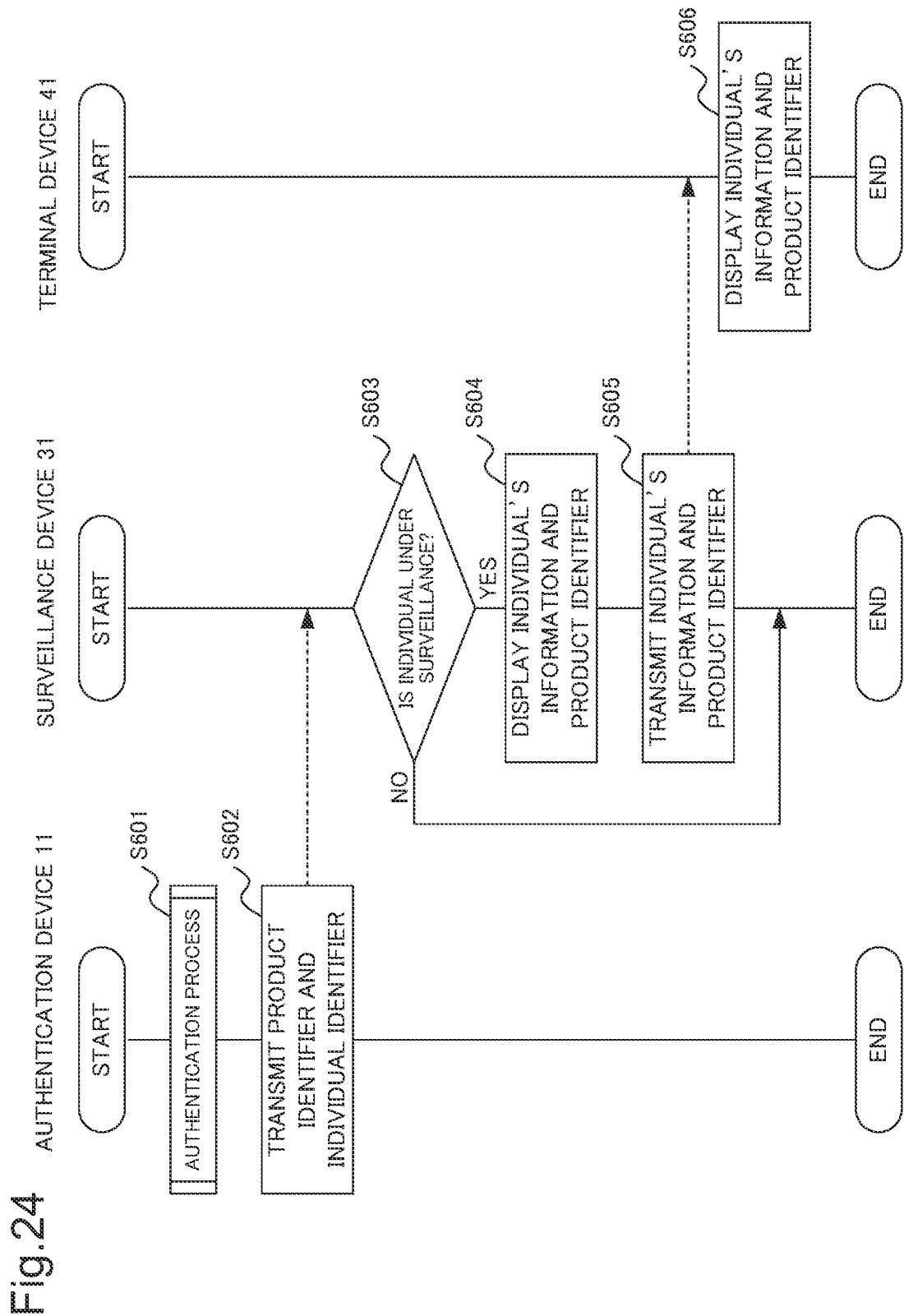
FIG. 24 is a flowchart showing a process in the surveillance system 6 according to the sixth example embodiment.

FIG. 24 is a flowchart showing a process in the surveillance system 6 according to the sixth example embodiment.

The authentication device 11 authenticates a subject by the same authentication process as in the first example embodiment (FIG. 6) (step S601).

The transmission unit 171 of the authentication device 11 transmits a product identifier and an individual identifier identified in the authentication process to the surveillance device 31 (step S602).

For example, the transmission unit 171 transmits the product identifier "P1" and the individual identifier "U1" to the surveillance device 31.

The surveillance device 31 determines whether the individual identifier received from the authentication device 11 is the individual identifier of an individual under surveillance (step S603). Here, when the individual identifier received from the authentication device 11 matches one of the individual identifiers in the surveillance information 311, the surveillance device 31 determines that the individual identifier received from the authentication device 11 is the individual identifier of an individual under surveillance.

For example, the surveillance device 31 refers to the surveillance information 311 in FIG. 22, and determines that the individual "U1" is under surveillance.

If it is determined in step S603 that the individual is under surveillance (step S603/YES), the surveillance device 31 displays, to an administrator or the like, information about the determined individual together with the product identifier received from the authentication device 11 (step S604).

Here, the surveillance device 31 refers to the surveillance information 311 and acquires information about the individual determined as a surveillance target.

For example, the surveillance device 31 refers to the surveillance information 311 in FIG. 22, and displays the information about the individual "U1" "Name: AAA, Sex: Male, Height: 170 cm, Weight: 60 kg" and the product "P1". Based on these pieces of information, the administrator or the like can collect a purchase history of the product "P1" and other commodities by the individual "U1" from stores selling the product "P1". Further, the administrator or the like can designate stores selling the product "P1", where the individual "U1" may visit, as places to be monitored by surveillance cameras or destinations to be staked out by investigators or the like.

The surveillance device 31 notifies notification destination terminal devices 41 of the information on the individual determined as the surveillance target, together with the product identifier received from the authentication device 11 (step S605). Here, the surveillance device 31 refers to the notification destination information 321, and notifies notification destination terminal devices 41 associated with the product identifier received from the authentication device 11, of the individual's information and the product identifier.

For example, the surveillance device 31 refers to the notification destination information 321 in FIG. 23, and notifies stores "S1", "S2", ... of the information about the individual "U1" "Name: AAA, ... " and the product "P1".

The terminal devices 41 display the individual's information and the product identifier received from the surveillance device 31 (step S606).

For example, the terminal device 41 in the store "S1" displays the information about the individual "U1" "Name: AAA, ... " and the product "P1". Based on these pieces of information, store employees or the like pay attention to whether a customer visiting the store or a customer who has purchased the product "P1" at the store is the individual "U1", and can notify the investigation agency such as the police when a customer believed to be the individual "U1" visits.

Thus, the operation of the surveillance system 6 according to the sixth example embodiment is completed.

As the authentication device 11 according to the sixth example embodiment, instead of the authentication device 11 according to the first example embodiment, the authentication device 13 or 14 according to the third or fourth example embodiment may be used.

In the sixth example embodiment, the identification of an individual may be performed by a method other than iris authentication. In this case, the authentication unit 151 of the authentication device 11 may identify an individual by a method other than iris authentication, such as face authentication or gait authentication.

According to the sixth example embodiment, information on a colored contact lens product being worn can be used for criminal investigation or the like. The reason is that the authentication device 11 transmits a product identifier and an individual identifier identified to the surveillance device 31, and the surveillance device 31 outputs the received product identifier if the received individual identifier is under surveillance.

While the disclosure has been particularly shown and described with reference to exemplary embodiments thereof, the disclosure is not limited to these embodiments. It will be understood by those of ordinary skill in the art that various changes in form and details may be made therein without departing from the spirit and scope of the example embodiments as defined by the claims.

Part or all of the above-described example embodiments may be described as in the following Supplementary Notes, but are not limited to the following.

(Supplementary Note 1)

An authentication device including:
 an image acquisition means for acquiring an image of an eye of a subject;
 an identification means for identifying a colored pattern of a colored contact lens worn by the subject by comparing a reference image with the image of the eye; and
 an authentication means for identifying the subject, using a feature in a region other than a colored region of the colored pattern in an iris region of the eye.

(Supplementary Note 2)

The authentication device according to Supplementary Note 1, in which
 the reference image is a colored pattern of one of a plurality of colored contact lens products, and
 the identification means identifies a product worn by the subject from the plurality of colored contact lens products by comparing a colored pattern of each of the plurality of products with the image of the eye, and identifies the colored pattern of the identified product as the colored pattern of the colored contact lens worn by the subject.

(Supplementary Note 3)

The authentication device according to Supplementary Note 2, further including:
 a storage means for storing an identifier for identifying an individual associated with an identifier for identifying a product and a feature in a region other than a colored region of a colored pattern of the product in an iris region of the individual,
 in which the authentication means identifies the subject by matching the feature in the region other than the colored region of the colored pattern of the identified product in the iris region of the subject against a feature in a region other than the colored region of the colored pattern of the identified product in the iris region of the individual stored in the storage means.

(Supplementary Note 4)

The authentication device according to Supplementary Note 2, further including:
 a storage means for storing an identifier for identifying a product associated with an identifier for identifying an individual who has worn the product,
 in which the authentication means extracts an individual associated with the identified product stored in the storage means, and identifies the subject from the extracted individual.

(Supplementary Note 5)

The authentication device according to Supplementary Note 1, in which
 the reference image is an image of one eye of both eyes of the subject,
 the image acquisition means acquires images of both eyes of the subject, and
 the identification means identifies the colored pattern of the colored contact lens worn by the subject by comparing the image of one eye of both eyes with the image of the other eye.

(Supplementary Note 6)

The authentication device according to any one of Supplementary Notes 1, 2, and 5, further including:

a storage means for storing an identifier for identifying an individual associated with a feature in an iris region of the individual, in which the authentication means identifies the subject by matching the feature in the region other than the colored region of the identified colored pattern in the iris region of the subject against the feature in the iris region of the individual stored in the storage means.

(Supplementary Note 7)

The authentication device according to any one of Supplementary Notes 1, 2, and 5, further including:

a storage means for storing an identifier for identifying an individual associated with an iris region of the individual, in which the authentication means identifies the subject by matching the feature in the region other than the colored region of the identified colored pattern in the iris region of the subject against a feature in a region other than the colored region of the identified colored pattern in the iris region of the individual stored in the storage means.

(Supplementary Note 8)

The authentication device according to any one of Supplementary Notes 2 to 4, further including:

a transmission means for transmitting, to an analysis device, an identifier for identifying the identified product and an identifier for identifying an individual identified as the subject, in which the analysis device performs analytical processing on an individual wearing a product, using the identifier of the product and the identifier of the individual received from the authentication device.

(Supplementary Note 9)

The authentication device according to Supplementary Note 8, in which as the analytical processing, the analysis device calculates, on each of the plurality of products, a total number of individuals wearing the product.

(Supplementary Note 10)

The authentication device according to Supplementary Note 8, in which as the analytical processing, the analysis device analyzes, on each of the plurality of products, a relationship between the product and an attribute of an individual wearing the product.

(Supplementary Note 11)

The authentication device according to Supplementary Note 10, in which the attribute of the individual is a commodity purchased by the individual, and the analysis device determines a commodity to be presented to the subject wearing the identified product, based on the analyzed relationship.

(Supplementary Note 12)

The authentication device according to any one of Supplementary Notes 2 to 4, further including:

a transmission means for transmitting, to a surveillance device, an identifier for identifying the identified product and an identifier for identifying an individual identified as the subject, in which the surveillance device stores an identifier for identifying an individual under surveillance, and outputs the identifier of the product received from the authentication device when the identifier of the individual received from the authentication device matches the identifier of the individual under surveillance.

(Supplementary Note 13)

The authentication device according to Supplementary Note 12, in which the surveillance device further stores the identifier for identifying the product associated with an identifier for identifying a notification destination, and notifies the notification destination associated with the identifier of the product received from the authentication device, of the identifier of the product when the identifier of the individual received from the authentication device matches the identifier of the individual under surveillance.

(Supplementary Note 14)

An authentication method including:

acquiring an image of an eye of a subject;

identifying a colored pattern of a colored contact lens worn by the subject by comparing a reference image with the image of the eye; and identifying the subject, using a feature in a region other than a colored region of the colored pattern in an iris region of the eye.

(Supplementary Note 15)

A computer-readable recording medium that causes a computer to execute a process including:

acquiring an image of an eye of a subject;

identifying a colored pattern of a colored contact lens worn by the subject by comparing a reference image with the image of the eye; and identifying the subject, using a feature in a region other than a colored region of the colored pattern in an iris region of the eye.

REFERENCE SIGNS LIST 1, 2, 3, 4 authentication system
5 analysis system
6 surveillance system
11, 12, 13, 14 authentication device
21 analysis device
31 surveillance device
41 terminal device
101 CPU
102 RAM
103 ROM
104 flash memory
105 communication I/F
106 display device
107 input device
108 camera
109 bus
111, 112 image acquisition unit
121, 122 identification unit
131 extraction unit
141 feature value calculation unit
151, 153, 154 authentication unit
161 display unit
171 transmission unit
181, 182, 183, 184 storage unit
211 product information
221, 223 authentication information
231 wearing information
311 surveillance information
321 notification destination information
500 eye
510 pupil
520 iris 600 colored contact lens
610 colored region

What is claimed is:

1. An authentication device comprising:
a memory configured to store instructions; and
at least one processor configured to execute the instructions to perform:
acquiring an image of an eye of a subject;
identifying a colored pattern of a colored contact lens worn by the subject by comparing a reference image with the image of the eye;
authenticating the subject, using a feature in a region other than a colored region of the colored pattern in an iris region of the eye, wherein the reference image is a colored pattern of one of a plurality of colored contact lens products;
identifying a product worn by the subject from the plurality of colored contact lens products by comparing a colored pattern of each of the plurality of products with the image of the eye, and identifying the colored pattern of the identified product as the colored pattern of the colored contact lens worn by the subject;
storing an identifier for identifying an individual associated with an identifier for identifying a product and a feature in a region other than a colored region of a colored pattern of the product in an iris region of the individual; and
identifying the subject by matching the feature in the region other than the colored region of the colored pattern of the identified product in the iris region of the subject against a feature in a region other than the colored region of the colored pattern of the identified product in the iris region of the individual stored in the storage.

2. The authentication device according to claim 1, further comprising:
a storage storing an identifier for identifying a product associated with an identifier for identifying an individual who has worn the product,
wherein the at least one processor is further configured to execute the instructions to perform:
extracting an individual associated with the identified product stored in the storage, and authenticating the subject from the extracted individual.

3. The authentication device according to claim 1, wherein
the reference image is an image of one eye of both eyes of the subject,
the at least one processor is configured to execute the instructions to perform:
acquiring images of both eyes of the subject, and
identifying the colored pattern of the colored contact lens worn by the subject by comparing the image of one eye of both eyes with the image of the other eye.

4. The authentication device according to claim 1, further comprising:
a storage storing an identifier for identifying an individual associated with a feature in an iris region of the individual,
wherein the at least one processor is configured to execute the instructions to perform:
identifying the subject by matching the feature in the region other than the colored region of the identified colored pattern in the iris region of the subject against the feature in the iris region of the individual stored in the storage.

5. The authentication device according to claim 1, further comprising:
a storage storing an identifier for identifying an individual associated with an iris region of the individual,
wherein the at least one processor is configured to execute the instructions to perform:
identifying the subject by matching the feature in the region other than the colored region of the identified colored pattern in the iris region of the subject against a feature in a region other than the colored region of the identified colored pattern in the iris region of the individual stored in the storage.

6. The authentication device according to claim 1, wherein:
the at least one processor is further configured to execute the instructions to perform:
transmitting, to an analysis device, an identifier for identifying the identified product and an identifier for identifying an individual identified as the subject,
wherein the analysis device performs analytical processing on an individual wearing a product, using the identifier of the product and the identifier of the individual received from the authentication device.

7. The authentication device according to claim 6, wherein
as the analytical processing, the analysis device calculates, on each of the plurality of products, a total number of individuals wearing the product.

8. The authentication device according to claim 6, wherein
as the analytical processing, the analysis device analyzes, on each of the plurality of products, a relationship between the product and an attribute of an individual wearing the product.

9. The authentication device according to claim 8, wherein
the attribute of the individual is a commodity purchased by the individual, and
the analysis device determines a commodity to be presented to the subject wearing the identified product, based on the analyzed relationship.

10. The authentication device according to claim 1, wherein:
the at least one processor is further configured to execute the instructions to perform:
transmitting, to a surveillance device, an identifier for identifying the identified product and an identifier for identifying an individual identified as the subject,
wherein the surveillance device
stores an identifier for identifying an individual under surveillance, and
outputs the identifier of the product received from the authentication device when the identifier of the individual received from the authentication device matches the identifier of the individual under surveillance.

11. The authentication device according to claim 10, wherein
the surveillance device further
stores the identifier for identifying the product associated with an identifier for identifying a notification destination, and
notifies the notification destination associated with the identifier of the product received from the authentication device, of the identifier of the product when the identifier of the individual received from the authentication device matches the identifier of the individual under surveillance.

12. An authentication method comprising:

acquiring an image of an eye of a subject;

identifying a colored pattern of a colored contact lens worn by the subject by comparing a reference image with the image of the eye;

authenticating the subject, using a feature in a region other than a colored region of the colored pattern in an iris region of the eye, wherein the reference image is a colored pattern of one of a plurality of colored contact lens products;

identifying a product worn by the subject from the plurality of colored contact lens products by comparing a colored pattern of each of the plurality of products with the image of the eye, and identifying the colored pattern of the identified product as the colored pattern of the colored contact lens worn by the subject;

storing an identifier for identifying an individual associated with an identifier for identifying a product and a feature in a region other than a colored region of a colored pattern of the product in an iris region of the individual; and identifying the subject by matching the feature in the region other than the colored region of the colored pattern of the identified product in the iris region of the subject against a feature in a region other than the colored region of the colored pattern of the identified product in the iris region of the individual stored in the storage.

13. A non-transitory computer-readable recording medium that causes a computer to execute a process comprising:

acquiring an image of an eye of a subject;

identifying a colored pattern of a colored contact lens worn by the subject by comparing a reference image with the image of the eye;

authenticating the subject, using a feature in a region other than a colored region of the colored pattern in an iris region of the eye, wherein the reference image is a colored pattern of one of a plurality of colored contact lens products;

identifying a product worn by the subject from the plurality of colored contact lens products by comparing a colored pattern of each of the plurality of products with the image of the eye, and identifying the colored pattern of the identified product as the colored pattern of the colored contact lens worn by the subject;

storing an identifier for identifying an individual associated with an identifier for identifying a product and a feature in a region other than a colored region of a colored pattern of the product in an iris region of the individual; and identifying the subject by matching the feature in the region other than the colored region of the colored pattern of the identified product in the iris region of the subject against a feature in a region other than the colored region of the colored pattern of the identified product in the iris region of the individual stored in the storage.

* * * * *